United States Patent
Saito et al.

(10) Patent No.: US 6,760,404 B2
(45) Date of Patent: Jul. 6, 2004

(54) RADIATION DETECTOR AND X-RAY CT APPARATUS

(75) Inventors: Yasuo Saito, Nasu-gun (JP); Hiroaki Miyazaki, Otawara (JP); Hiroshi Aradate, Otawara (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 10/117,103

(22) Filed: Apr. 8, 2002

(65) Prior Publication Data

US 2002/0110216 A1 Aug. 15, 2002

Related U.S. Application Data

(62) Division of application No. 09/718,482, filed on Nov. 24, 2000.

(30) Foreign Application Priority Data

Dec. 24, 1999 (JP) .......................................... 11-366180
Dec. 24, 1999 (JP) .......................................... 11-368273

(51) Int. Cl.[7] .................................................. G01T 1/24
(52) U.S. Cl. ...................... 378/98.8; 378/4; 250/370.09
(58) Field of Search ............................ 378/4, 19, 98.8, 378/86; 250/370.09, 370.08, 580

(56) References Cited

U.S. PATENT DOCUMENTS

| | | | |
|---|---|---|---|
| 5,032,728 A | | 7/1991 | Chang et al. |
| 5,319,206 A | | 6/1994 | Lee et al. |
| 5,566,218 A | * | 10/1996 | Nobuta et al. ................. 378/20 |
| 5,629,524 A | * | 5/1997 | Stettner et al. ........ 250/370.09 |
| 5,635,718 A | | 6/1997 | DePuydt et al. |
| 5,692,507 A | | 12/1997 | Seppi et al. |
| 5,694,446 A | | 12/1997 | Shinohara |
| 5,786,597 A | | 7/1998 | Lingren et al. |
| 6,198,791 B1 | * | 3/2001 | He et al. ....................... 378/19 |

\* cited by examiner

Primary Examiner—Edward J. Glick
Assistant Examiner—Hoon Song
(74) Attorney, Agent, or Firm—Oblon, Spivak, McClelland, Maier & Neustadt, P.C.

(57) ABSTRACT

A radiation detector includes a plurality of detector modules detachably mounted on a detector base. Each of the detector modules has a plurality of element blocks permanently mounted on a module base. Each element block has a plurality of radiation detection elements formed on a signal substrate in the form of an m×n matrix. A detector module is made up of a plurality of element blocks. A radiation detector is made up of a plurality of detector modules. This makes it possible to tile many detection elements and manufacture a radiation detector with a wide field of view.

21 Claims, 20 Drawing Sheets

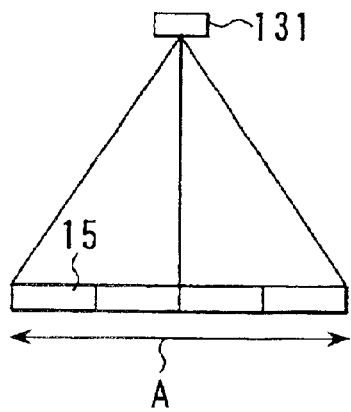 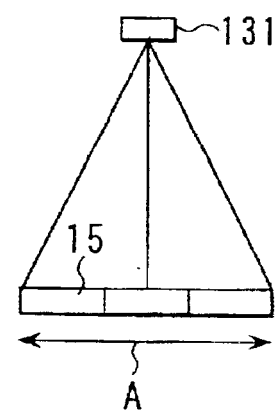
FIG. 9A    FIG. 9B
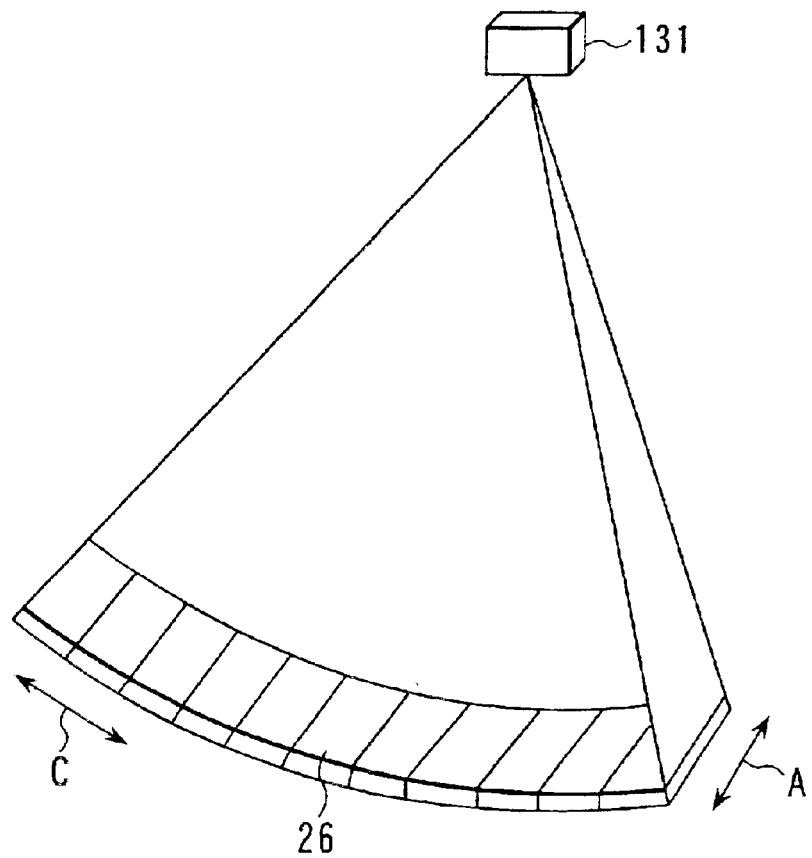
FIG. 9C

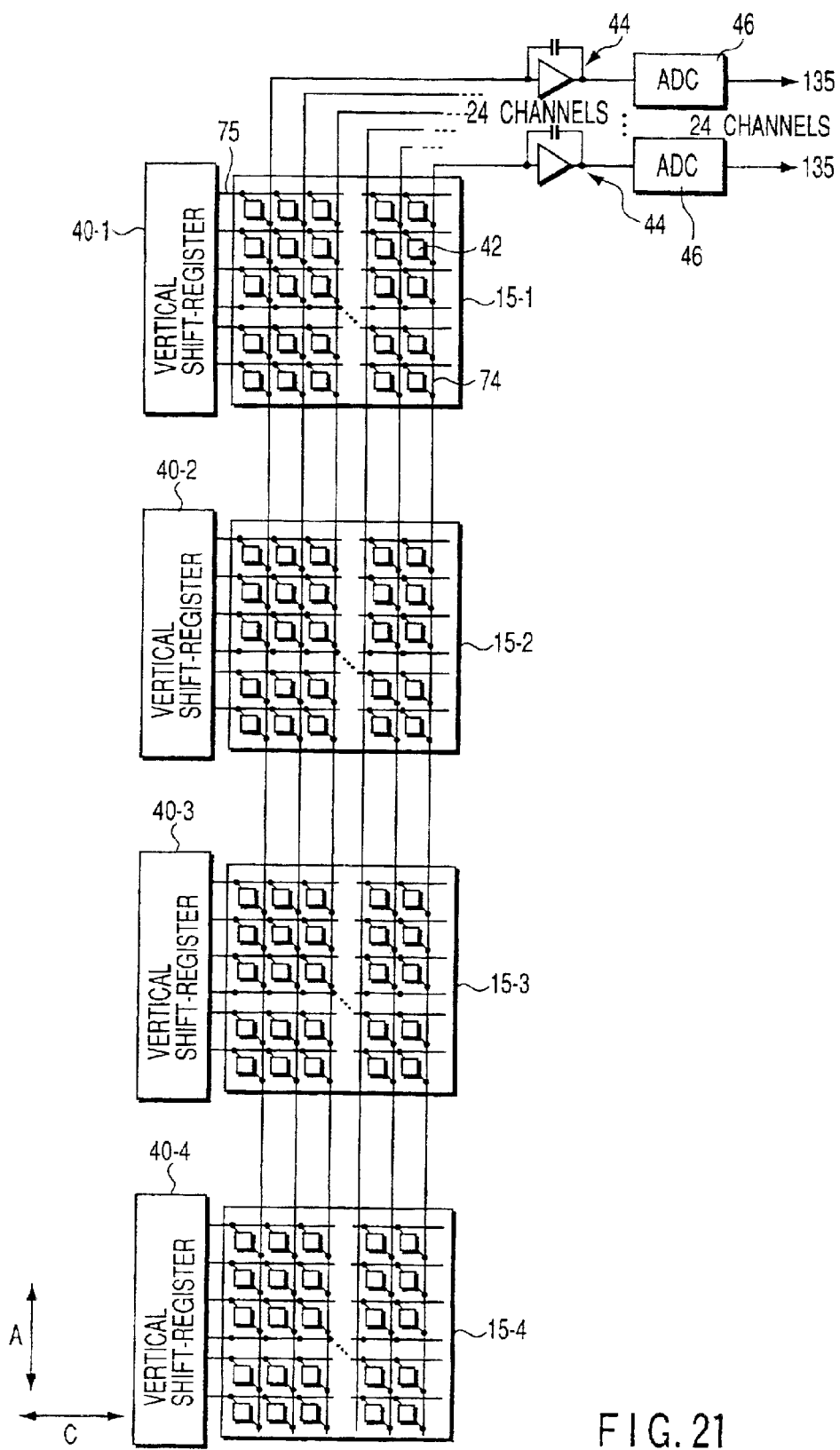
F I G. 21

RADIATION DETECTOR AND X-RAY CT APPARATUS

CROSS-REFERENCE TO RELATED APPLICATIONS

This application is based upon and claims the benefit of priority from the prior Japanese Patent Applications No. 11-366180, filed Dec. 24, 1999; and No. 11-368273, filed Dec. 24, 1999, the entire contents of which are incorporated herein by reference.

BACKGROUND OF THE INVENTION

The present invention relates to a 2D array type radiation detector having a plurality of detection elements in the form of a matrix which detect radiations such as x-rays as electrical signals, and an x-ray CT apparatus.

A medical x-ray CT apparatus has an x-ray tube and detector. X-rays generated by the x-ray tube are transmitted through an object to be examined and incident on the detector. The detector has a plurality of detection elements for detecting radiations such as x-rays as electrical signals. Detection elements can be classified into indirection conversion type elements, each designed to convert an x-ray into light by a phosphor (scintillator) and further convert the light into an electrical signal by a photoelectric conversion element (photodiode), and direct conversion type apparatuses, each using specific semiconductor characteristic, i.e., a photoconduction phenomenon in which electron-hole pairs are generated in a semiconductor and moved to its electrode by using x-rays. It is expected that direct conversion type apparatuses, which can achieve reductions in size, weight, and profile, will become popular.

As detectors for x-ray CT, single-slice type detectors are widely used. A single-slice type detector has a plurality of detection elements arrayed in a line. A multislice type detector constituted by single-slice type detectors arranged in a plurality of lines is also known.

FIG. 1 is a partial sectional view of a conventional multislice type detector. FIG. 2 is a schematic plan view of the detector. Referring to FIG. 2, an illustration of a scintillator is omitted. A plurality of photodiodes 92 are arranged on the rear surface of a scintillator 97. The plurality of photodiodes 92 are respectively connected to a plurality of integrators 95 through a plurality of wires 91. Selection switches 96 are provided in units of lines. Outputs from the integrators 95 are sequentially read out through the selection switches 96. The outputs of the selection switches 96 are electrically connected to a substrate 94 through bonding wires 93.

The integrators 95 store the signals detected by the photodiodes 92. Integral signals are sequentially output to the substrate 94 by the selection switches 96 through the bonding wires 93. The reason why the integral signals are sequentially read out by the selection switches 96 is that the number of bonding wires that can be formed on the substrate 94 is limited.

A great deal of attention has been paid to a 2D array type detector as a next-generation detector, which has more channels than the above multislice type detector, with the element pitch in the vertical direction (slice direction) being equal to the element pitch in the horizontal direction (channel direction).

To put this 2D array type detector into practice, various problems must be solved.

First, as the number of detection elements greatly increases as in the 2D array type detector, the precision in tiling the many elements into a specific shape deteriorates.

Second, as the number of detection elements greatly increases as in the 2D array type detector, the probability of the occurrence of faulty detection elements increases, and hence the yield decreases.

Likewise, as the detector is used for a long period of time, it is inevitable that some of many detection elements will fail. In this case, a detection element array or the overall detector must be replaced, resulting in a high cost. This is the third problem.

In addition, signal sampling is performed in CT an enormous number of times, e.g., several hundred or thousand times, per rotation. Therefore, the time permitted for 1-period signal read operation is very short. It is very difficult to complete reads of signals from many channels within such a short period of time. This is the fourth problem.

BRIEF SUMMARY OF THE INVENTION

It is an object of the present invention to provide a radiation detector which implements tiling of many detection elements in the form of a matrix.

A radiation detector includes a plurality of detector modules detachably mounted on a detector base. Each of the detector modules has a plurality of element blocks permanently mounted on a module base. Each element block has a plurality of radiation detection elements formed on a signal substrate in the form of an m×n matrix. A detector module is made up of a plurality of element blocks. A radiation detector is made up of a plurality of detector modules. This makes it possible to tile many detection elements and manufacture a radiation detector with a wide field of view.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 9A is a side view showing an array of element blocks in the first embodiment;

FIG. 9B is a side view showing another array of element blocks in the first embodiment;

FIG. 9C is a perspective view showing an array of detector modules in the first embodiment;

FIG. 21 is an equivalent circuit diagram of one detector module in the first embodiment;

DETAILED DESCRIPTION OF THE INVENTION

Preferred embodiments of the present invention will be described in detail below with reference to the views of the accompanying drawing.

(First Embodiment)

Figure 1:
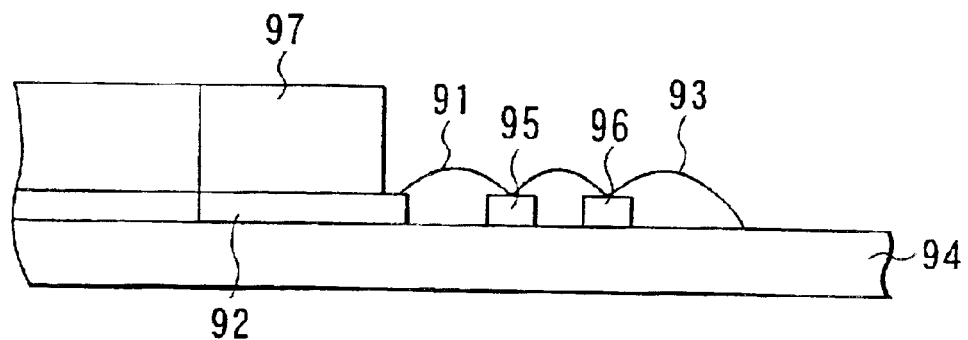
FIG. 1 is a partial sectional view of a detector in the prior art.
Figure 2:
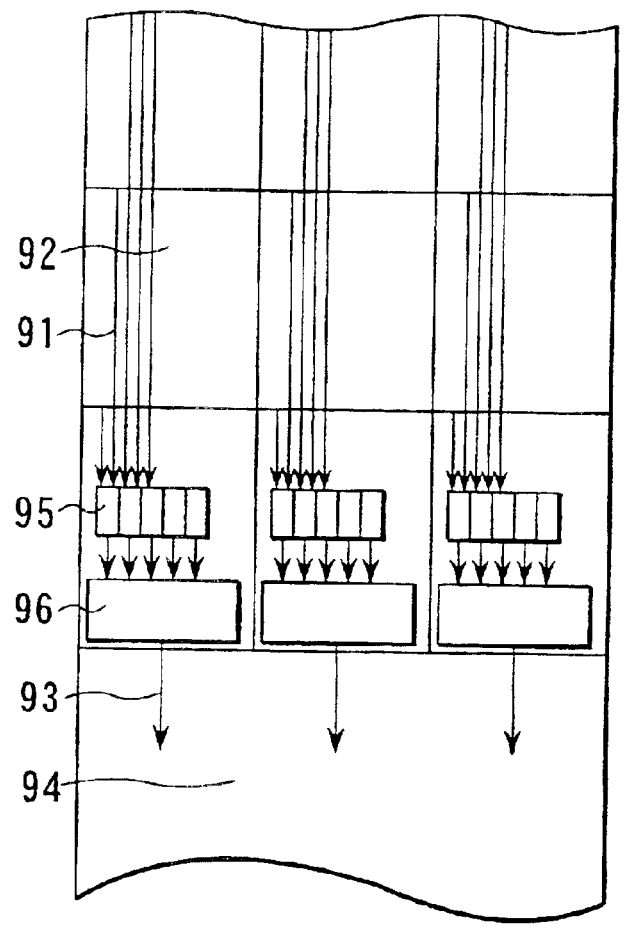
FIG. 2 is a view showing the arrangement of bonding wires connected to the detector in the prior art.
Figure 3:
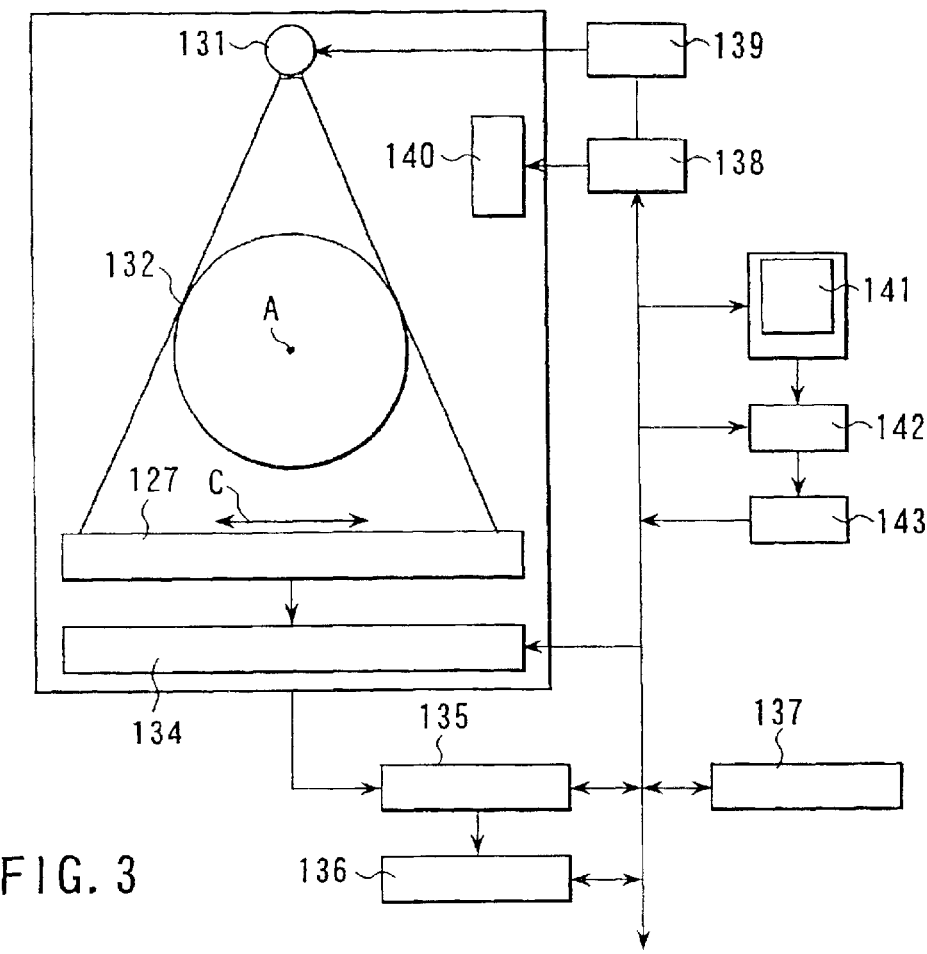
FIG. 3 is a system diagram of an x-ray CT apparatus according to the first embodiment of the present invention.

FIG. 3 is a system diagram of an x-ray CT apparatus according to the first embodiment.

An x-ray tube 131 is supported, together with a radiation detector 127, to be rotatable around an object 132 to be examined. The x-ray tube 131 generates a so-called x-ray cone beam spreading in two directions, namely a channel direction C and a slice direction A (direction parallel to the rotation axis (direction perpendicular to the drawing surface)). The x-ray beam transmitted through the object 132 is detected by the radiation detector 127. The signal detected by the radiation detector 127 is sent to a data processing unit 135 for performing correction processing and the like through a data acquisition circuit 134 to undergo predetermined signal processing. The resultant data is temporarily stored in a storing unit 136. The following components are connected to a host controller 138: a high-voltage generator 139 for supplying power to the x-ray tube 131, a gantry driving unit 140 for a rotating gantry that rotates the x-ray tube 131 and the like, a reconstructing unit 137 for reconstructing data, a display unit 141 for displaying the image reconstructed by the reconstructing unit 137, an operation unit 142 for operating the display unit 141, an input device 143 for sending a control signal from the operation unit 142 to the host controller 138, and the like.

Figure 4:
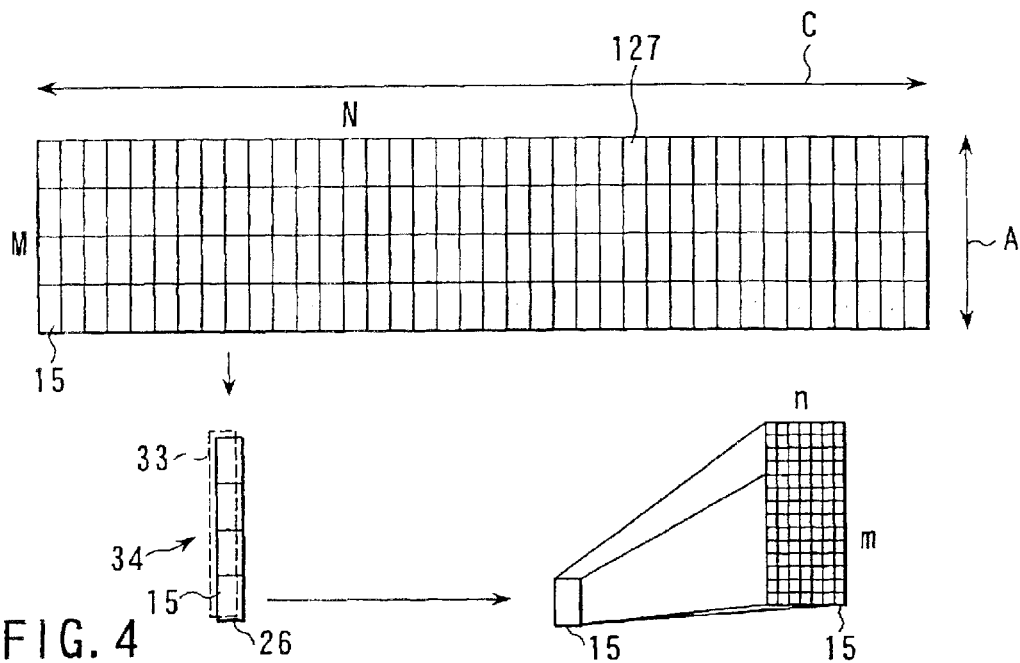
FIG. 4 is a plan view showing the schematic structure of a radiation detector 127 in FIG. 3.

FIG. 4 schematically shows the structure of the radiation detector 127. The radiation detector 127 is comprised of a plurality of, e.g., 38, detector modules 34 arrayed along the channel direction C. In x-ray CT, the 38 detector modules 34 are not arrayed flat but are arrayed in the form of an arc centered on the focal point of the x-ray tube 131. One detector module 34 is made up of one element module 26 and one collimator module 33. Each element module 26 is made up of a plurality of, e.g., four, element blocks 15 arrayed along the slice direction A. One element block 15 has m×n detection elements in the form of a matrix formed on a single substrate, together with peripheral circuits. In this case, one detection element is handled as one channel. Obviously, however, a predetermined number of neighboring detection elements may be handled as one channel. The number of channels per block is set in accordance with, for example, a matrix size of 24×64, which exhibits relatively high yield in manufacturing semiconductor devices.

In the block manufacturing stage, the element blocks 15 are inspected one by one, and defective products are eliminated. A plurality of, e.g., four, element blocks 15 are arrayed along the slice direction A and fixed on a module base (an element 18 in FIG. 10A). Note that the four coupled element blocks 15 will be referred to as the element module 26. The collimator module 33 is mounted on the element module 26, thus completing the detector module 34. The element modules 15 can not be disassembled. The detector is assembled, tested, repaired, and replaced in units of detector modules 34.

The 38 detector modules 34 are arrayed on a curved detector base 28 (FIG. 10B), thus completing the radiation detector 127. Each of the 38 detector modules 34 is detachably mounted on the detector base. If, therefore, a given detector module 34 fails, the radiation detector 127 can be inexpensively and quickly restored by replacing only the faulty detector module with a normal detector module 34.

Note that the radiation detector 127 may be formed by arraying the element blocks 15 in two orthogonal directions, namely the directions A and C, without using the element modules 26. However, this detector is preferably handled in units of modules 34 in consideration of operation efficiency and yield.

Figure 5:
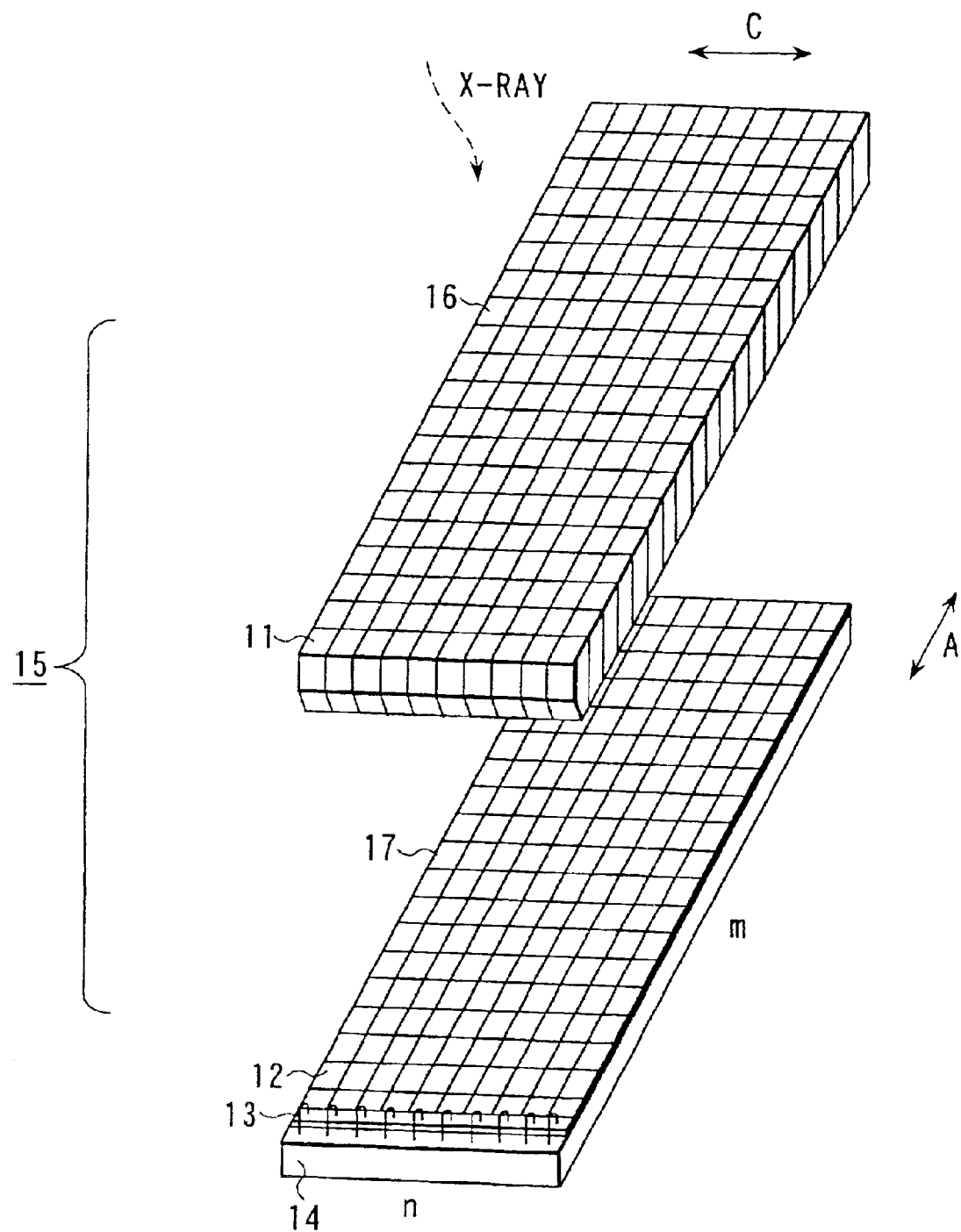
FIG. 5 is a view showing the structure of an element block 15 in FIG. 4.
Figure 6:
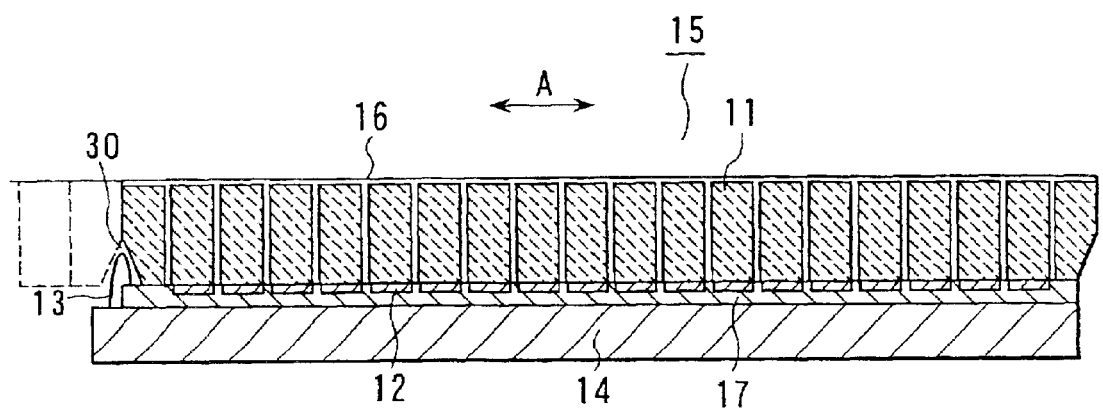
FIG. 6 is a partial sectional view of the element block 15 in FIG. 4.

FIG. 5 is an exploded perspective view of the element block 15. FIG. 6 is a sectional view of this block. Photodiodes 17 are formed of an m×n matrix, and mounted on the upper surface of a substrate 14. A scintillator block 16 is mounted on the photodiodes 17. The scintillator block 16 is made up of m×n scintillator pieces 11 equal in number to the matrix of photodiodes 17.

A side surface and x-ray incident surface of each scintillator piece 11 are coated with a light reflecting material. The light reflecting material blocks external light and prevents leakage of light generated by each scintillator piece 11. In place of the light reflecting material coat, white plastic plates may be bonded to the side surface and x-ray incident surface of each scintillator piece 11.

Most of the scintillator pieces 11 have rectangular parallelepiped shapes, typically cubic shapes. As shown in FIG. 6, however, n scintillator pieces 11 located on the two ends in the slice direction A have end faces each notched, obliquely and inwardly, from its substantially middle point to the bottom surface so as to have a substantially pentagonal cross-section. A bonding wire 13 for connecting the photodiode 17 to the substrate 14 is accommodated in the space secured by a notched portion 30. With this structure, as shown in FIGS. 9A and 9B, when the four element blocks 15 are joined to each other along the slice direction A to form the element module 26, the scintillator pieces 11 of the adjacent element blocks 15 can be brought into tight contact with each other, thus eliminating any gaps between the blocks. In addition, since each bonding wire 13 extends from an end portion in the slice direction A, when the detector modules 34 are arrayed in the channel direction C, all gaps between the modules can be eliminated, as shown in FIG. 9C.

Figure 7:
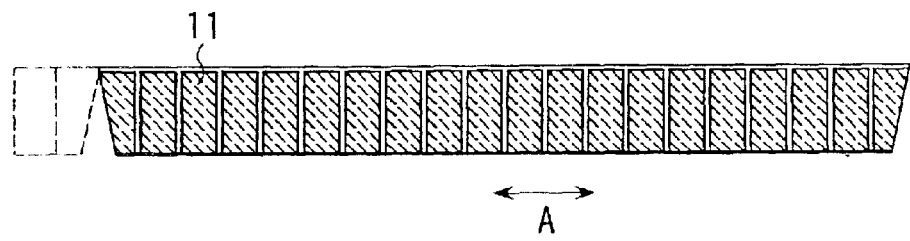
FIG. 7 is a partial sectional view showing another shape of a notched portion in FIG. 6.
Figure 8:
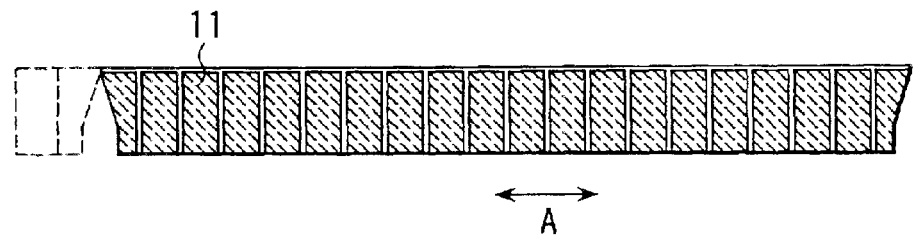
FIG. 8 is a partial sectional view showing still another shape of the notched portion in FIG. 6.

Note that the shape of each notched portion 30 is not specifically limited. For example, as shown in FIG. 7, an end face of the scintillator piece 11 may be obliquely notched from the upper surface to the bottom surface. In this case, the scintillator piece 11 on the corresponding end has a trapezoidal cross-section. Alternatively, an end face of the scintillator piece 11 may be notched in a proper curve instead of being notched straight, as shown in FIG. 8.

The surface area of the element block 15 (substrate 14) is designed to be almost equal to the x-ray incident surface area of the scintillator block 16. The scintillator blocks 16 are designed to have almost the same size. Note that the size of the photodiodes 17 located on the two ends in the slice direction A may be designed to be slightly smaller than the size of the remaining photodiodes 17 in consideration of a joint margin. In this case, the channels at the ends of each element module 26 in the slice direction A tend to greatly differ in x-ray conversion ratio from the remaining channels. However, this problem can be solved by causing a data processing unit 35 to perform data correction such as weighted interpolation for the data detected by the channels at the ends. Weights are set in consideration of the purpose of inspection, the precision of data obtained by the elements at the ends, expected resolution, and the like.

The signal detected by each photodiode 17 is sent as an electrical signal to the substrate 14 through the bonding wire 13. Owing to problems in boding techniques, the bonding wire 13 protrudes from the surface of a photodiode 12 to some extent. The protruding bonding wire 13 is accommodated in the space defined by the notched portions 30 of the two element blocks 15 adjacent to each other in the slice direction A.

Figure 10A:
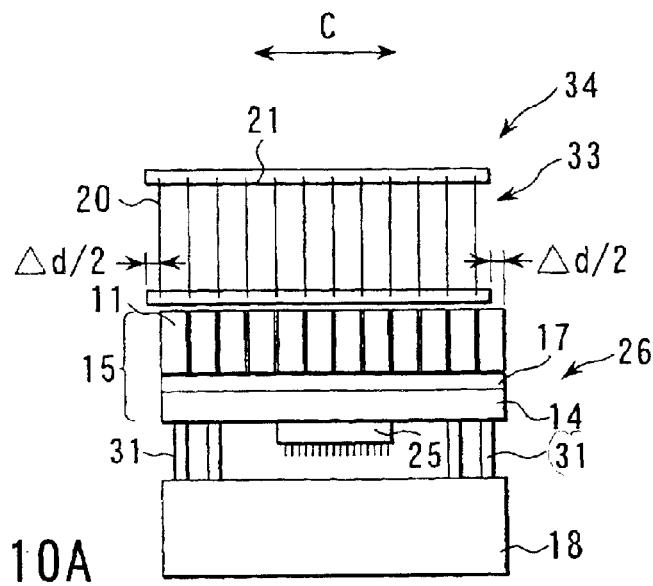
FIG. 10A is a view showing the side surface structure of a detector module in the first embodiment.
Figure 10B:
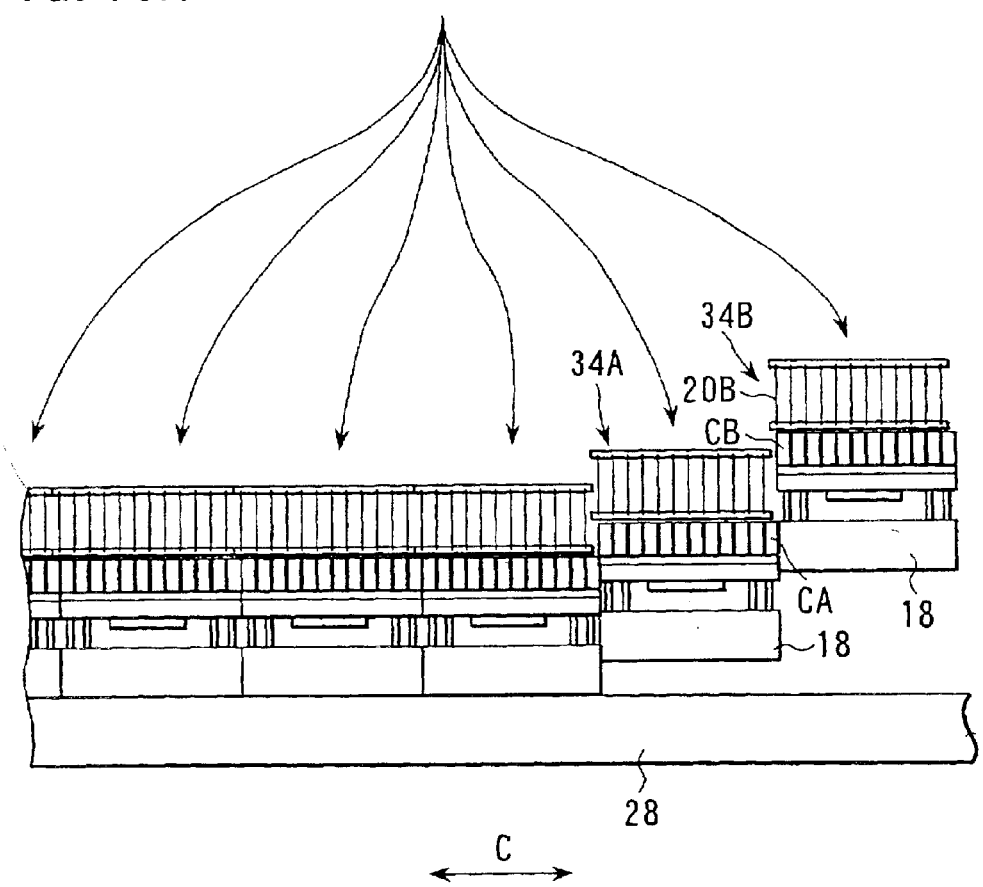
FIG. 10B is a side view showing an array of the detection modules shown in FIG. 10A.
Figure 11:
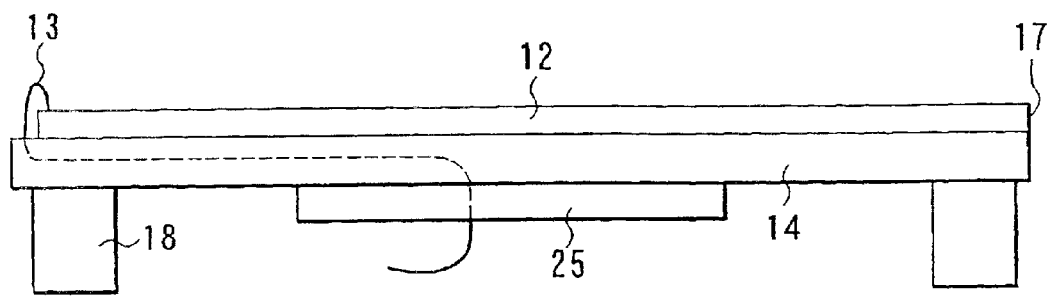
FIG. 11 is a sectional view showing a substrate and its peripheral portion in FIG. 10A.

FIG. 10A is a side view showing one detector module 34 when viewed from the slice direction. As described above, one detector module 34 is comprised of one element module 26 made up of the four element blocks 15 coupled to each other in the slice direction and one collimator module 33 mounted on the element module 26. The element module 26 is fixed on a plate-like module base 18 through a fixing stand 31. A data acquisition circuit board 25 for reading out signals from the photodiodes 17 and acquiring signals is placed on the element module 26, which is secured by the poles 31. The signal sent from each photodiode 17 to the substrate 14 through the bonding wire 13 is sent to the data acquisition circuit board 25 of a data acquisition unit 143 placed on the lower surface of the board through an interconnection in the board, as shown in FIG. 11. Note that this circuit 25 may be formed on the substrate 14 of the photodiode 17, together with a photodiode array and its peripheral circuit.

The collimator module 33 has a plurality of collimator plates 20 each made of a heavy metal with high stiffness such as tungsten or molybdenum. The plurality of collimator plates 20 are supported between two collimator supports 21 to be arrayed parallel at intervals equal to the pitch of channels. The collimator module 33 is positioned with respect to the element module 26 such that the plurality of collimator plates 20 are respectively positioned on the boundaries between a plurality of channels.

The width of the collimator module 33 in the channel direction C is designed to be almost equal to that of the element module 26. The collimator module 33 is not aligned with the element module 26 but is shifted from the element module 26 in the channel direction C by a distance (Δd/2) ½ a distance (pitch) Ad between the central points of the adjacent detection elements (channels). By shifting the collimator module 33 from the element module 26 by the distance (Δd/2), the collimator plate 20 can be positioned immediately above the boundary between the channels of the adjacent element modules 26. With this arrangement, when the 38 detector modules 34 are arrayed in a line on a detector base 28. The collimator plate 20B can be positioned between a channel CA on the right end of a given module 34A and a channel CB on the left end of an adjacent module 34B on the right. Thus the scatterd radiation remorment can be implemented at the boundary.

By sequentially placing the modules 34 having the same structure in the channel direction C in this manner, the gaps between the modules 34 can be eliminated.

As described above, each of the 38 detector modules 34 can be easily detached from the detector base 28 by relatively easy operation, e.g., unfastening a few screws. With this arrangement, when a given detector module 34 fails, the faulty module is detached from the detector base 28, and a new normal module 34 is mounted in the empty space, thereby restoring the normal function of the radiation detector 127.

Note that when the faulty module 34 is to be replaced, since the collimator module 33 overlaps the adjacent modules 34, the faulty module 34 cannot be detached alone, a plurality of normal modules 34 on the right side of the faulty module 34 must also be detached.

Figures 12A, 12B:
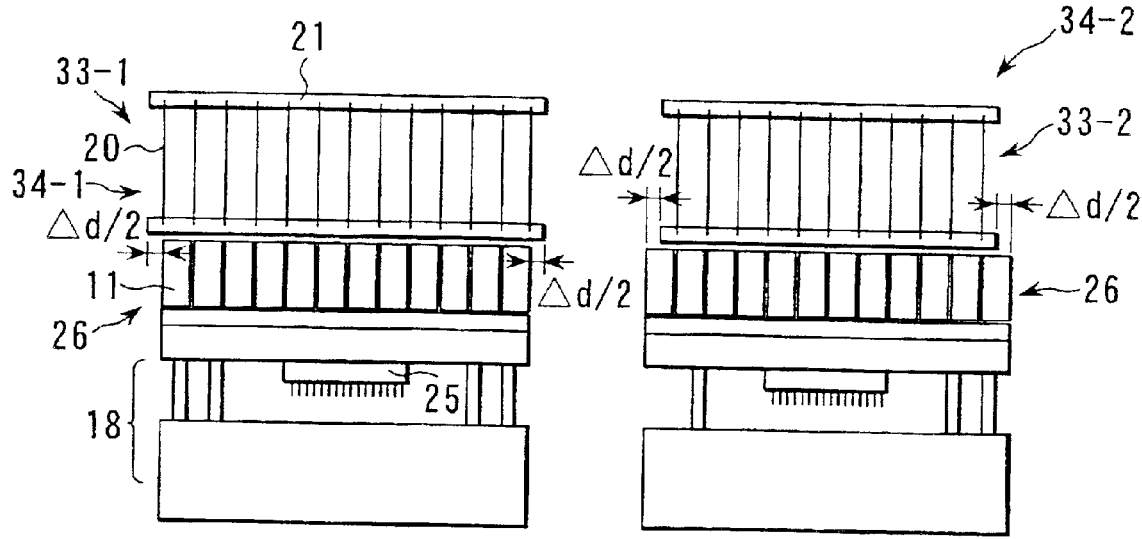
FIG. 12A is a view showing another side surface structure of the detector module in the first embodiment.
FIG. 12B is a view showing the side surface structure of a detector module paired with the detector module in FIG. 12A.
Figure 12C:
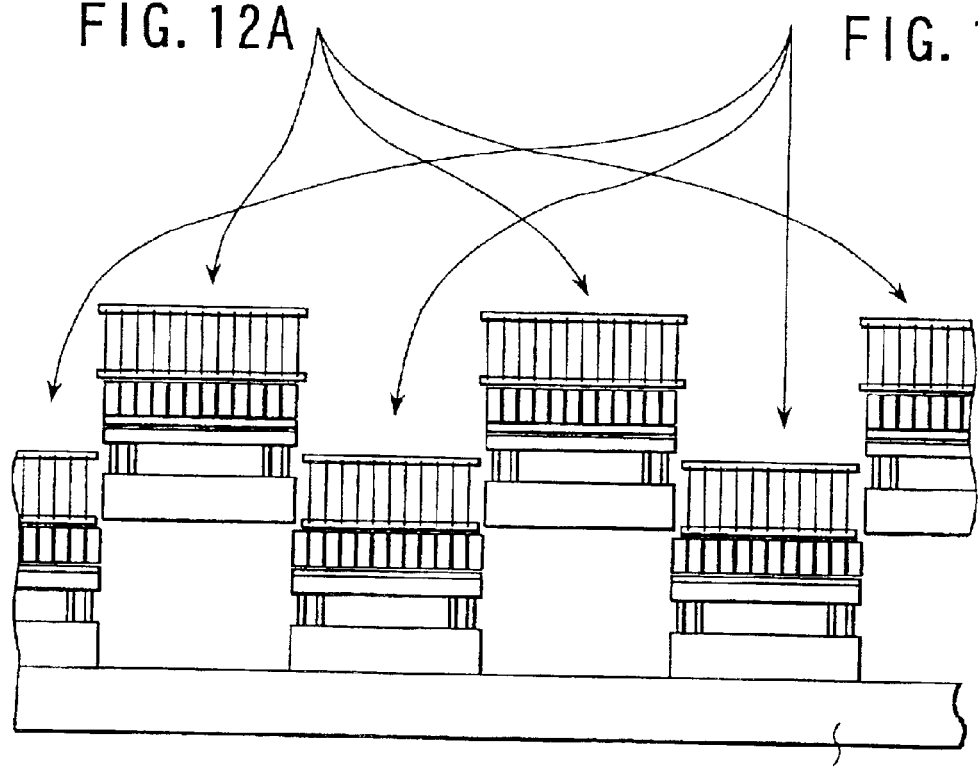
FIG. 12C is a side view showing an array of the detector modules in FIG. 12A and the detector modules in FIG. 12B.

FIGS. 12A, 12B, and 12C show a modification configured to improve the efficiency of replacing operation by decreasing the number of detector modules 34 to be detached when the faulty module 34 is to be replaced with a normal module 34. For this purpose, two types of detector modules 34-1 and 34-2 are prepared. The two types of detector modules 34-1 and 34-2 have the same structure except for the widths of collimator modules 33-1 and 33-2 and the numbers of collimator plates 20. As shown in FIG. 12A, in one collimator module 33-1, the number of collimator plates 20 is larger than the number of channels (n) by one. As shown in FIG. 12B, in the other collimator module 33-2, the number of collimator plates 20 is smaller than the number of channels (n) by one. One collimator module 33-1 is wider than the other collimator module 33-2 by a width corresponding to the difference (two) between the numbers of collimator plates 20.

Two types of detector modules 34 whose collimator modules 33-1 and 33-2 differ in this manner are alternately arranged on the detector base 28 without any gap along the channel direction C, as shown in FIG. 12C.

This structure requires two types of detector modules 34. However, when a faulty module is to be replaced with a normal module 34, the number of detector modules 34 to be detached can be decreased to one or three. When the faulty module 34 in FIG. 12A is to be replaced, only the faulty module 34 is detached, and a normal module 34 is attached. When the faulty module 34 in FIG. 12B is to be replaced, the two adjacent modules 34 on the two sides of the faulty module 34 are detached, together with the faulty module 34, and a normal module 34 is attached. Thereafter, the two adjacent modules 34 are placed back into position.

Figure 13:
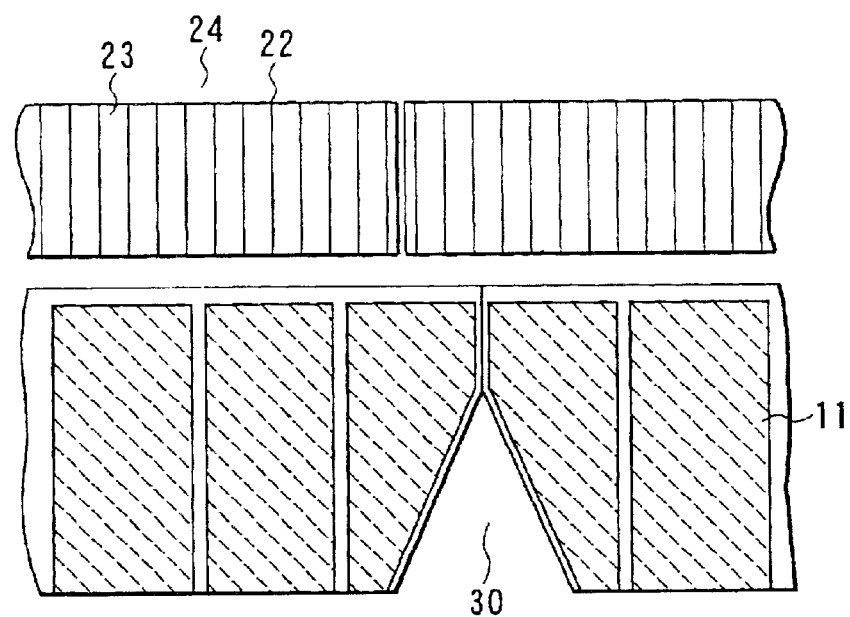
FIG. 13 is a side view showing a grid substituting a collimator.

Note that a grid may be used in place of a collimator. FIG. 13 is an enlarged view of a portion near the grid and a scintillator. A grid 24 is formed by alternately stacking and bonding metal foils 22 made of a heavy metal such as lead and intermediate members 23 made of a light metal such as aluminum. Since the metal foil 22 is supported by the intermediate member 23, any supports like the collimator supports 2 are not required.

Figure 14:
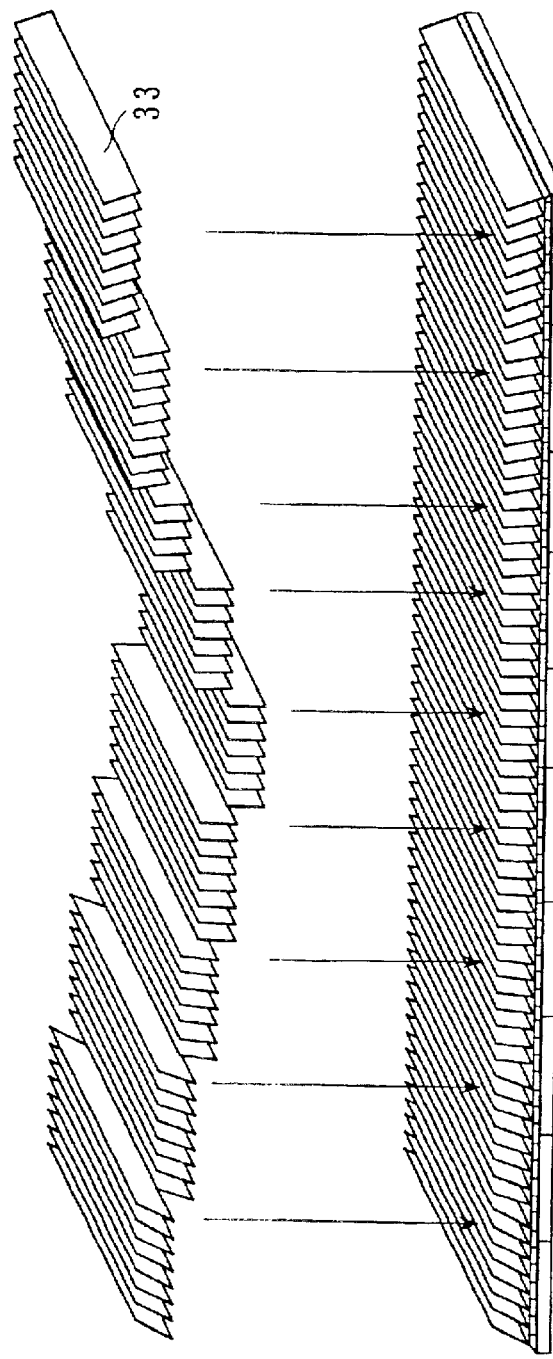
FIG. 14 is a view showing an example of how a plurality of collimator modules are mounted in the first embodiment.

Note that collimators may be completed by arraying the detector modules 34 on which the collimator modules 33 are mounted. As shown in FIG. 14, after the detector modules 34 on which no collimator modules 33 are mounted are arrayed, the collimator modules 33 may be mounted on the detector modules 34. Alternatively, collimators completed by coupling the collimator modules 33 may be mounted on the arrayed detector modules 34.

As described above, by notching portions of the scintillator pieces 11 on the ends and placing extraction means such as the bonding wires 13 in the notched portions, a large radiation detector without any gap can be formed, which is required to, for example, require temporally continuous voxel data.

Figure 15:
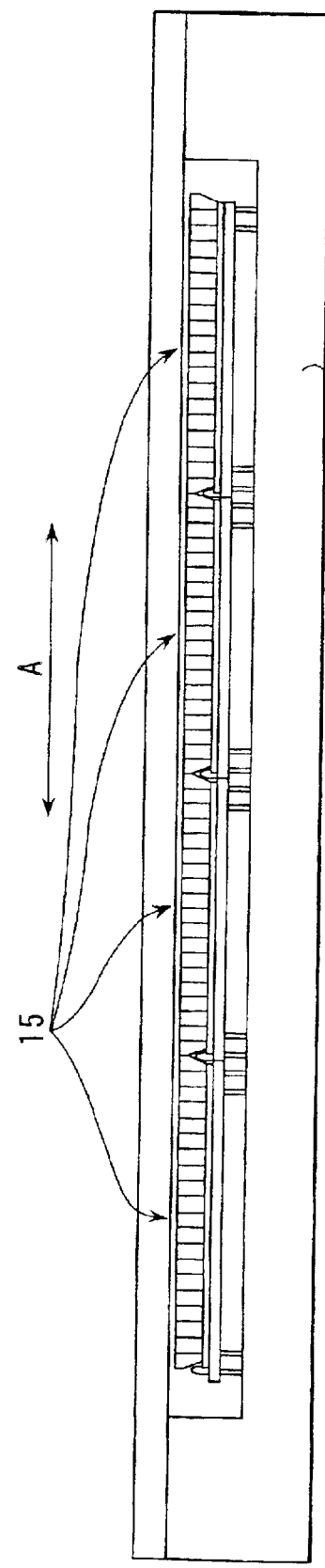
FIG. 15 is a cross-sectional view of a detector according to the first embodiment.

For example, in the prior art, only four channels can be arrayed in the slice direction A. As shown in FIG. 15, according to the present invention, 256 channels can be implemented in the slice direction by arraying four element blocks 15 each having m (e.g., 64) photodiodes in the slice direction A. More channels can be implemented by increasing the number of element blocks 15 arrayed or arraying a plurality of element modules 26 along the slice direction A.

In the overall detector, M×N (256×912) channels can be implemented by arraying four element blocks 15, each having m×n (64×24) photodiodes, in the slice direction A, and 38 element blocks 15 in the channel direction C. Note that m may be an even number, e.g., m=64, or may be an odd number, e.g., m=65. The number represented by m is not limited to a specific value. In addition, the number of element blocks in the channel direction C is may be an even number, e.g., n=24, or an odd number, e.g., n=25. Similar to m, the number represented by n is not limited to a specific value. Likewise, the number of detector modules is not limited to an even or odd number.

If the number of element blocks 15 in the slice direction A is an even number, e.g., four as shown in FIG. 9B, the center line of an x-ray beam generated by the x-ray tube 131 in the slice direction A passes through the joint portion between the element block 15 and another element block. If the number of element blocks 15 in the slice direction A is an odd number, e.g., three as shown in FIG. 9C, the center line of an x-ray beam generated by the x-ray tube 131 passes through the center of the element block 15.

Figure 16:
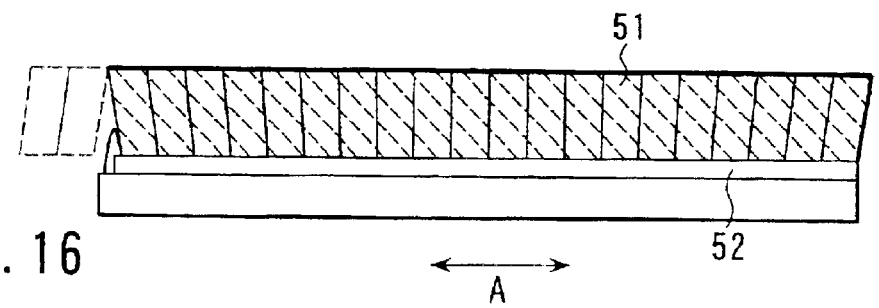
FIG. 16 is a side view showing another scintillator piece in the first embodiment.

According to the above description, each scintillator piece has a rectangular parallelepiped shape. However, as shown in FIG. 16, a scintillator piece 51 having a substantially parallelogrammic cross-section whose upper side on the x-ray incident surface side is slightly longer than the lower side on the light output surface side may be used, or a scintillator piece having a trapezoidal cross-section whose light output surface is narrower than the x-ray incident surface may be used. In addition, a photodiode 52 is positioned and shaped to oppose the light output surface of each scintillator piece 51. Since other arrangements are the same as in the first embodiment, a description thereof will be omitted.

In this case, since the scintillator pieces other than those on the two ends also have shapes other than rectangular parallelepiped shapes, the method of manufacturing a scintillator block is complicated. However, the light incident surfaces of the photodiodes joined to the scintillator pieces on the two ends of the scintillator block can be made almost equal in size to those of the photodiodes joined to the scintillator pieces other than those on the two ends, and hence the precision of data detected at the two ends can be improved. Alternatively, a plurality of scintillator pieces may be selected from those on the ends, and each selected scintillator piece may have a shape whose x-ray incident surface is narrow than the light output surface.

In this case, since the scintillator pieces and photodiodes other than those on the two ends of the element block change in shape, the x-ray conversion efficiency may greatly vary. In this case, therefore, data precision can be improved by performing data correction such as weighted interpolation for the data detected by all the scintillator photodiodes as well in the data processing unit 35. Weights should be set in consideration of the purpose of an inspection, the precision of data obtained by the elements on the ends, expected resolution, and the like.

Figure 17:
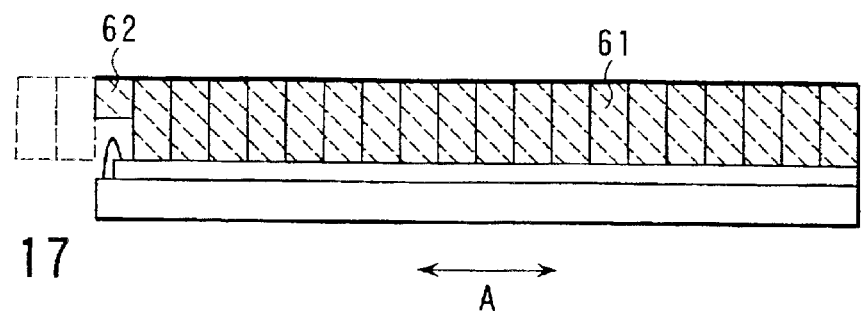
FIG. 17 is a side view showing still another scintillator piece in the first embodiment.

Furthermore, in the arrangement shown in FIG. 17, each scintillator piece 61 has a substantially rectangular parallelepiped shape whose x-ray incident surface is almost equal in size to the light output surface as described above, but a dummy scintillator 62 formed on each end is thinner than the remaining scintillator pieces. The x-ray incident surface of each dummy scintillator 62 is almost equal in size to the x-ray incident surface of the scintillator piece 61, but the length of a side surface of the dummy scintillator 62 is shorter than that of the scintillator piece 61. The dummy scintillator 62 is formed to, for example, shield the bonding wire 13 against x-rays so as to prevent a malfunction. As the dummy scintillator 62, a general scintillator that is made lightproof, a scintillator that has almost the same arrangement as that of a general scintillator but is modified to emit no light, a scintillator made of a heavy metal, or the like is used. Note that the dummy scintillator pieces 62 are positioned/mounted such that the x-ray incident surfaces of the scintillator pieces 61 and dummy scintillators 62 become almost flush with each other.

The length of each dummy scintillator 62 in the channel direction may be equal to that of the scintillator block 16. In this case, the length of a side surface of the dummy scintillator 62 remains unchanged, but the length of the x-ray incident surface of the dummy scintillator 62 in the slice direction is equal to the length of the 61 in the slice direction, and the length in the channel direction is equal to the length of the scintillator block 16.

In this case, since the respective scintillator pieces and photodiodes have almost the same shape and size, the respective scintillator pieces and photodiodes are likely to exhibit the same x-ray conversion ratio. However, since no photodiodes are used for the dummy scintillators 62, no data can be acquired from the dummy scintillators 62. If, therefore, a plurality of element blocks 15 are arrayed in the slice direction A, data acquisition omission portions are present between the element blocks. In this case, therefore, the data precision can be improved by performing weighted interporation such that omitted data is obtained by averaging data acquired by photodiodes adjacent to each data acquisition omission portion in the slice direction A or photodiodes adjacent to the adjacent photodiodes in the channel direction C. The range of data and weights used for interpolation are set in consideration of the purpose of inspection, the precision of data obtained by the elements at the ends, expected resolution, and the like.

As described above, the method using dummy scintillators can be practiced by only adding shielding means to a conventional scintillator block, and hence is very versatile.

Figure 18:
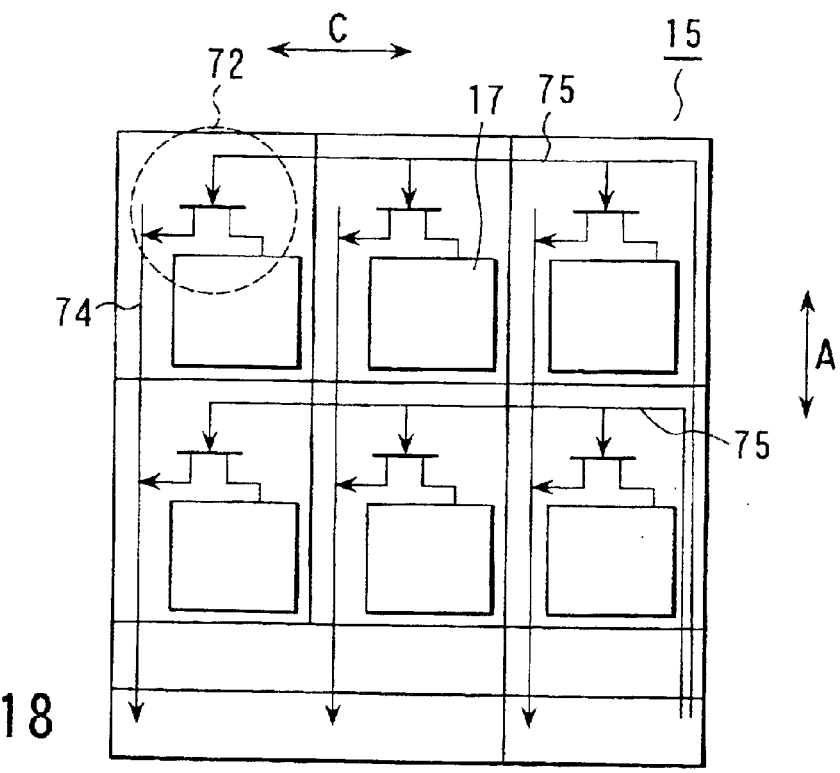
FIG. 18 is an equivalent circuit diagram of a detection element in the first embodiment.

FIG. 18 is a circuit diagram of a portion of the element block 15. The element block 15 has a plurality of photodiodes 17 arranged in the form of an m×n matrix. Signal lines 74 are connected to the outputs of the photodiodes 17 through a plurality of transistor switches 72. The outputs of m photodiodes 17 arrayed in a line along the slice direction A are commonly connected to the same signal line 74. The gates of n transistor switches 72 arrayed in the channel direction C are commonly connected to the same control line 75.

When an x-ray beam strikes a given scintillator piece 11, the x-ray beam is converted into light by the scintillator piece 11. This light is converted into an electrical signal by the corresponding photodiode 17. While the transistor switch 72 is off, charges are stored in the photodiode 17. A plurality of control lines 75 are sequentially activated. A plurality of switches 72 are sequentially tuned on in synchronism with the above operation. A plurality of switches 75 are sequentially tuned on in the slice deirection A and tuned on in the channel deirection C in a parallel. As a consequence, pieces of charge information in a plurality of slices are serially read out. In the prior art, one signal line is connected to each photodiode. If, however, a plurality of photodiodes in a slice line in each channel are commonly connected to a signal line, the number of signal lines can be greatly reduced.

When one slice is to be constituted by a predetermined number of adjacent photodiodes, analog signal addition can be implemented by simultaneously turning on the switches 72 of connected to the adjacent control line 75. Thereby data partially added in a slice can be output.

Figure 19:
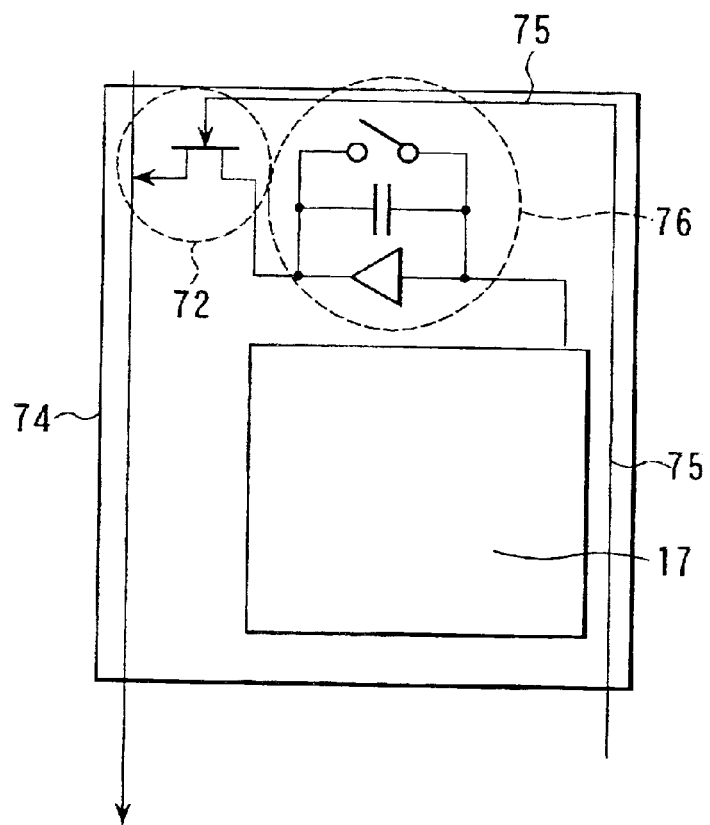
FIG. 19 is another equivalent circuit diagram of a detection element in the first embodiment.

FIG. 19 shows another arrangement of a portion of the element block 15. An integrator 76 is interposed between the photodiode 17 and the transistor switch 72. As each integrator 76, a type of integrator having an amplifier connected in parallel with a capacitor or another type of integrator is used.

Since an output from each photodiode is an analog current signal. To perform signal processing for such a signal in a general computer, this current signal is converted into a voltage signal, and the voltage signal is converted into a digital signal. In the case shown in FIG. 19, the integrator 76 between the photodiode 17 and the transistor switch 72 performs current/voltage conversion. This eliminates the necessity to provide any current/voltage conversion circuit for the data acquisition circuit board 25. In addition, the response speed increases. Furthermore, since the path of an output from the amplifier of the integrator 76 elongates, and the path of data input to the amplifier which is susceptible to disturbances such as noise shortens, resulting in an increase in resistance to disturbances such as noise.

Figure 20:
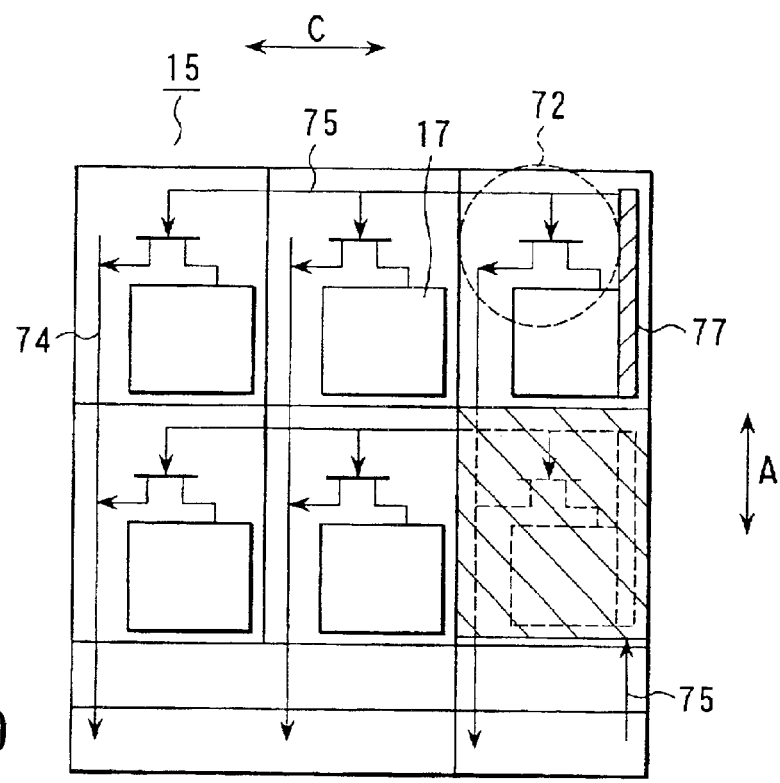
FIG. 20 is still another equivalent circuit diagram of a detection element in the first embodiment.

As shown in FIG. 20, a control signal generating circuit 77 is formed on a corner of the element block 15. Referring to FIG. 20, an illustration of an scintillator in the direction of the drawing surface is omitted, only a portion of the scintillator is indicated by the hatching to explain the positional relationship between the scintillator and other elements. The switch 72 and control signal generating circuit 77 are hidden behind the scintillator when viewed from the x-ray tube 131, thereby preventing a malfunction and damage due to radiation of x-rays. Forming the control signal generating circuit 77 on the corner of the element block 15 eliminates the necessity to form a plurality of interconnections for supplying control signals from the outside of the element block to a plurality of control signals 75. Since only a few control signal is required to be supplied from the outside of the element block to the control signal generating circuit 77, the arrangement of interconnections can be simplified.

Signal read operation according to an embodiment of the present invention will be described next. FIG. 21 is a schematic circuit diagram showing one detector module of the radiation detector 127 and a portion of the data acquisition circuit 134 which corresponds to one module. As described above, one detector module 34 has four element blocks 15-1, 15-2, 15-3, and 15-4 arrayed in the slice direction. Assume that in each of the element blocks 15-1, 15-2, 15-3, and 15-4, a plurality of detection elements 42, each constituted by the scintillator piece 11 and photodiode 17, are arranged in the form of a 24×64 matrix.

In each of the element blocks 15-1, 15-2, 15-3, and 15-4, 24 signal lines 74 and 64 control lines are arranged in columns and rows, and the detection elements 42 are respectively arranged on the intersections of the lines. The outputs of the photodiodes 17 of the 64 detection elements 42 arrayed in a slice line in each channel are connected to the common signal lines 74 through the 64 transistor switches. These signal lines 74 are connected to each other between the element blocks. The 24 signal lines 74 are connected to each amplifier 44. The gates of 24 element transistors arrayed in a channel line in each slice are commonly connected to the 64 control lines 75.

Figure 22:
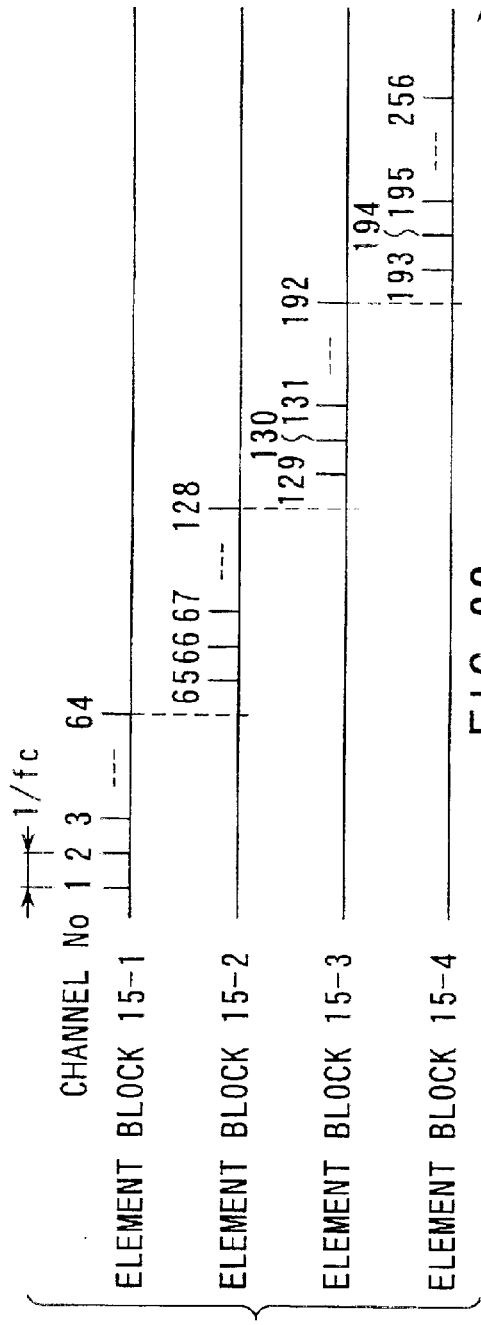
FIG. 22 is a view showing a signal read sequence for one line of detector modules in FIG. 21.

A vertical shift-register 40-1, 40-2, 40-3 and 40-4 sequentially supplies pulses to the 64×4 control lines 75 across the four element blocks 15-1, 15-2, 15-3, and 15-4. With this operation, as shown in FIG. 22, signals are sequentially read out from the 64×4 detection elements 42 arranged in a slice line in each channel to the amplifier 44 converted into voltage signals by an amplifier 44 connected to the output line 47, and are further converted into digital signals by an analog/digital converter (ADC) 46. This operation is executed the first signal line 74—the 24th signal line 74 in parallel. Such signal read operation in the 38 detector modules 34 are executed in parallel.

Figure 23:
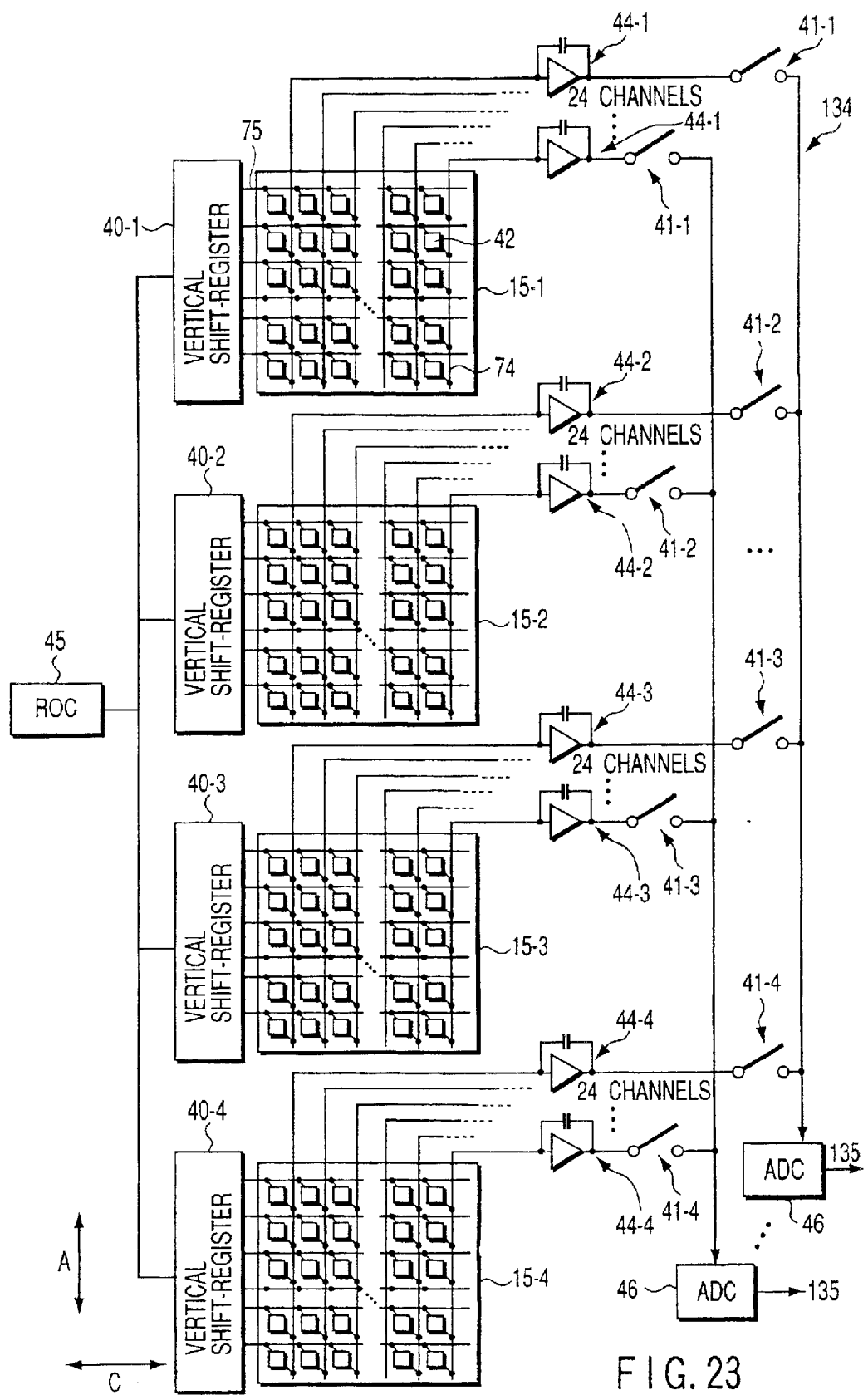
FIG. 23 is another equivalent circuit diagram of one detector module in the first embodiment.
Figure 25:
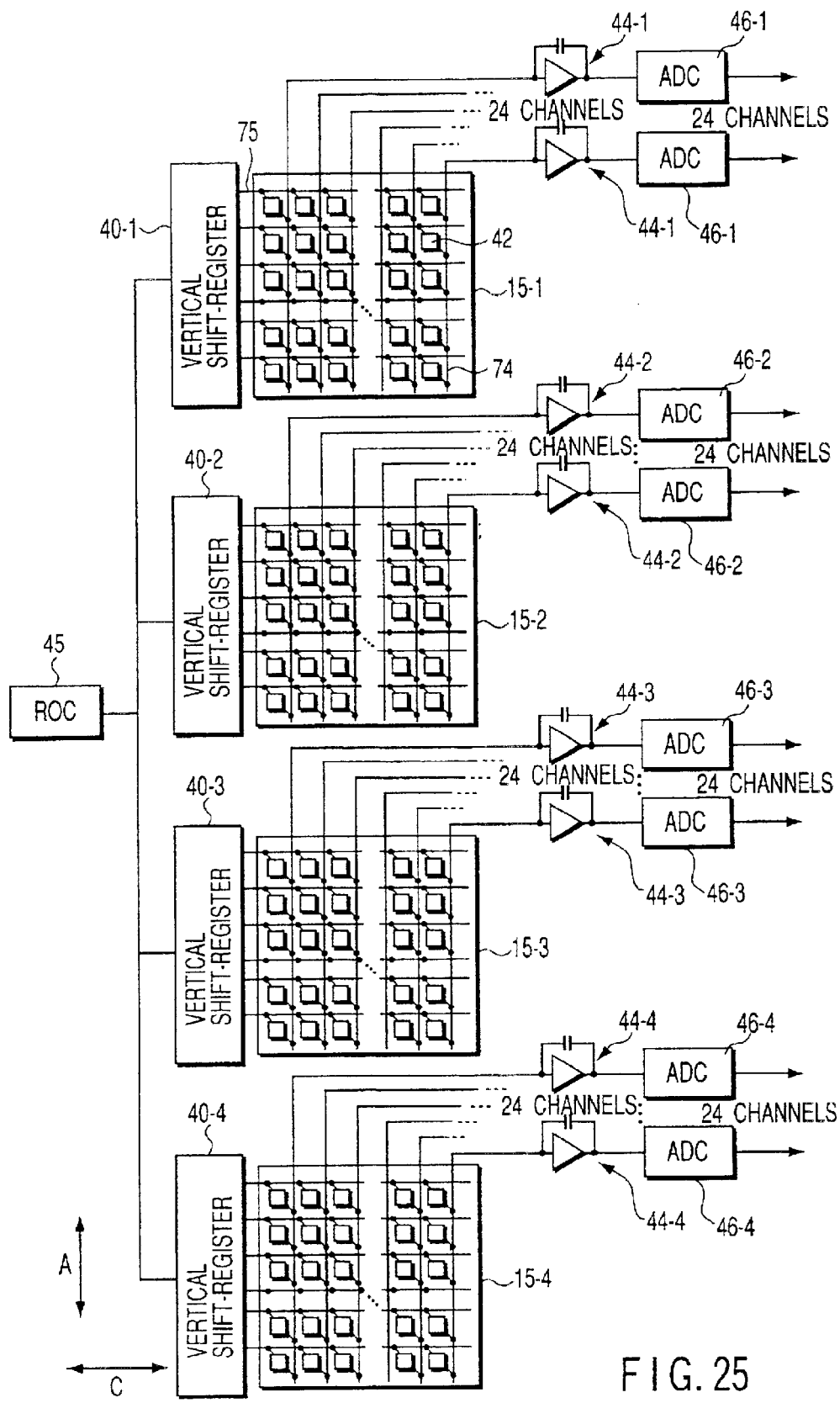
FIG. 25 is still another equivalent circuit diagram of one detector module in the first embodiment.

FIG. 23 shows another arrangement of the detector module 34. In this case, the signal lines 74 are not connected between the element blocks, and output bus lines 47-1, 47-2, 47-3, and 47-4, and amplifiers 44-1, 44-2, 44-3, and 44-4 are respectively provided for the element blocks 15-1, 15-2, 15-3, and 15-4. Outputs from the amplifiers 44-1, 44-2, 44-3, and 44-4 are output through switches 41-1, 41-2, 41-3 and 41-4 and the common analog/digital converter 46. The switches 41-1, 41-2, 41-3 and 41-4 are sequentially operated.

Figure 24:
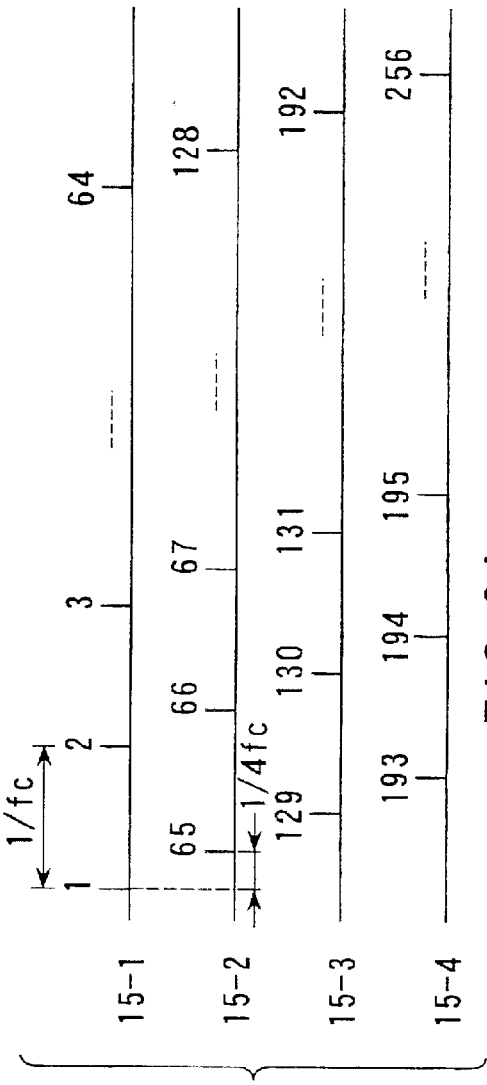
FIG. 24 is a view showing a signal read sequence for one line of detector modules in FIG. 23.

A readout pulses for amplifiers 44-1, 44-2, 44-3 and 44-4 sequentially supplies to these being shifted from each other by ¼ the time of a data period (1/fc). With this operation, as shown in FIG. 24, signal read operation is performed in accordance with the interleaving scheme. More specifically, signal reads of the photodiodes 17 of the three element blocks 15-2, 15-3, and 15-4 are interleaved between a signal read of a given photodiode 17 of the element block 15-1 and a signal read of the adjacent photodiode 17 in the slice direction A. This scheme can realize high-speed read operation.

In addition, signals may be parallelly read out from the four element blocks 15-1, 15-2, 15-3, and 15-4 in one detector module 34 by respectively providing analog/digital converters 46-1, 46-2, 46-3, and 46-4 for the element blocks 15-1, 15-2, 15-3, and 15-4.

(Second Embodiment)

This embodiment relates to an x-ray CT apparatus (x-ray computed tomography apparatus; CT scanner) equipped with the 2D array type radiation detector having a large field of view according to the first embodiment. Note that x-ray CT apparatuses include various types, e.g., a rotate/rotate type which an x-ray tube and radiation detector integrally rotate around an object, and a stationary/rotate type in which many detection elements are arrayed in the form of a ring, and only the x-ray tube rotates around an object. The present invention can be applied to any type. This embodiment will be described below as a rotate/rotate type of apparatus that has currently become mainstream. To reconstruct 1-volume voxel data (or one tomographic image), projection data corresponding to one rotation about the object, i.e., about 360°, is required. In a half-scan method, projection data corresponding to about 210 to 240° is required. The present invention can be applied to either of these schemes. Assume that 1-volume voxel data (or one sheet of a tomographic image) is reconstructed from projection data corresponding to about 360° as in the former general scheme.

Figure 26:
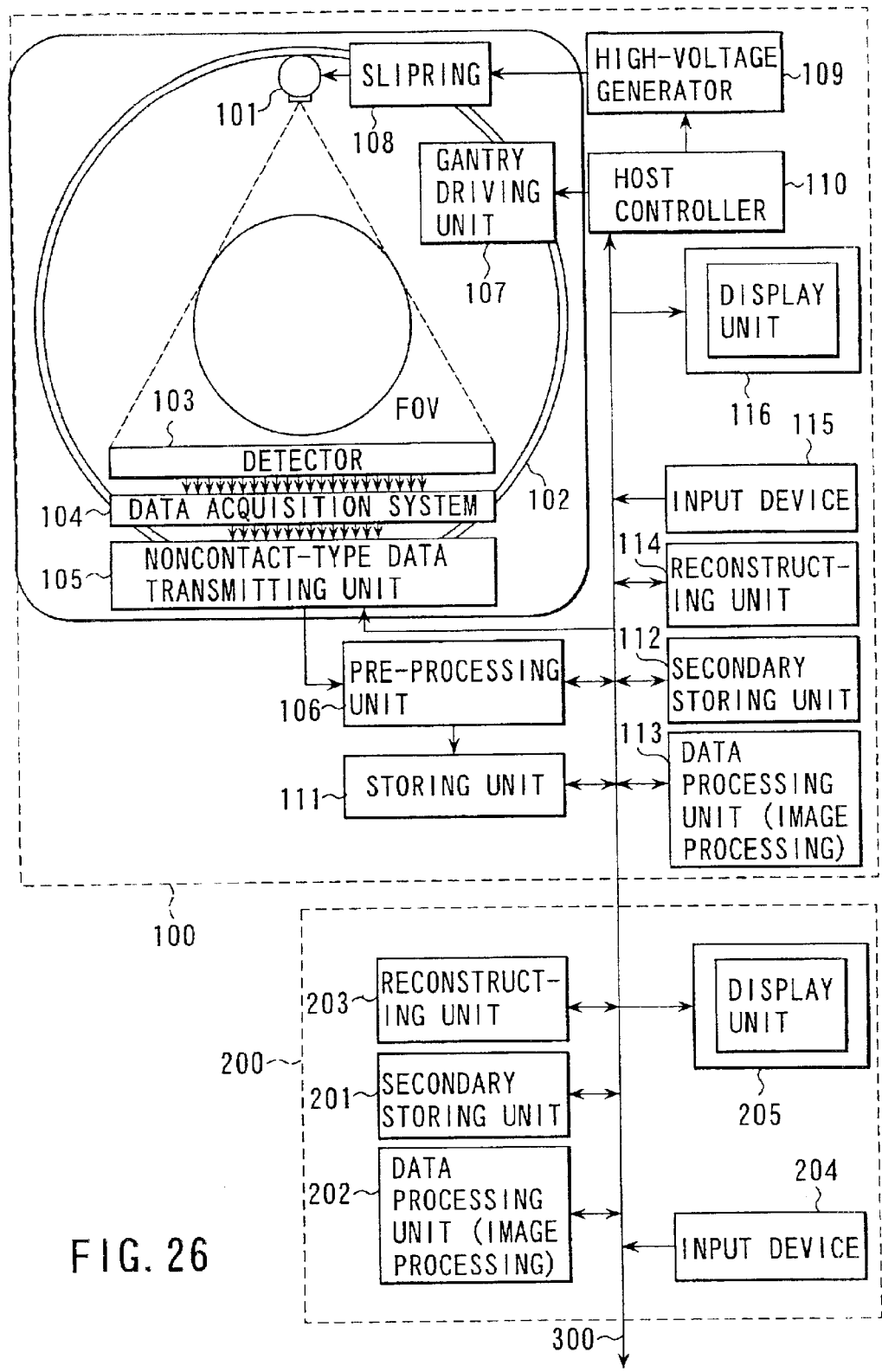
FIG. 26 is a view showing the arrangement of an x-ray CT scanner according to the second embodiment of the present invention.
Figure 27:
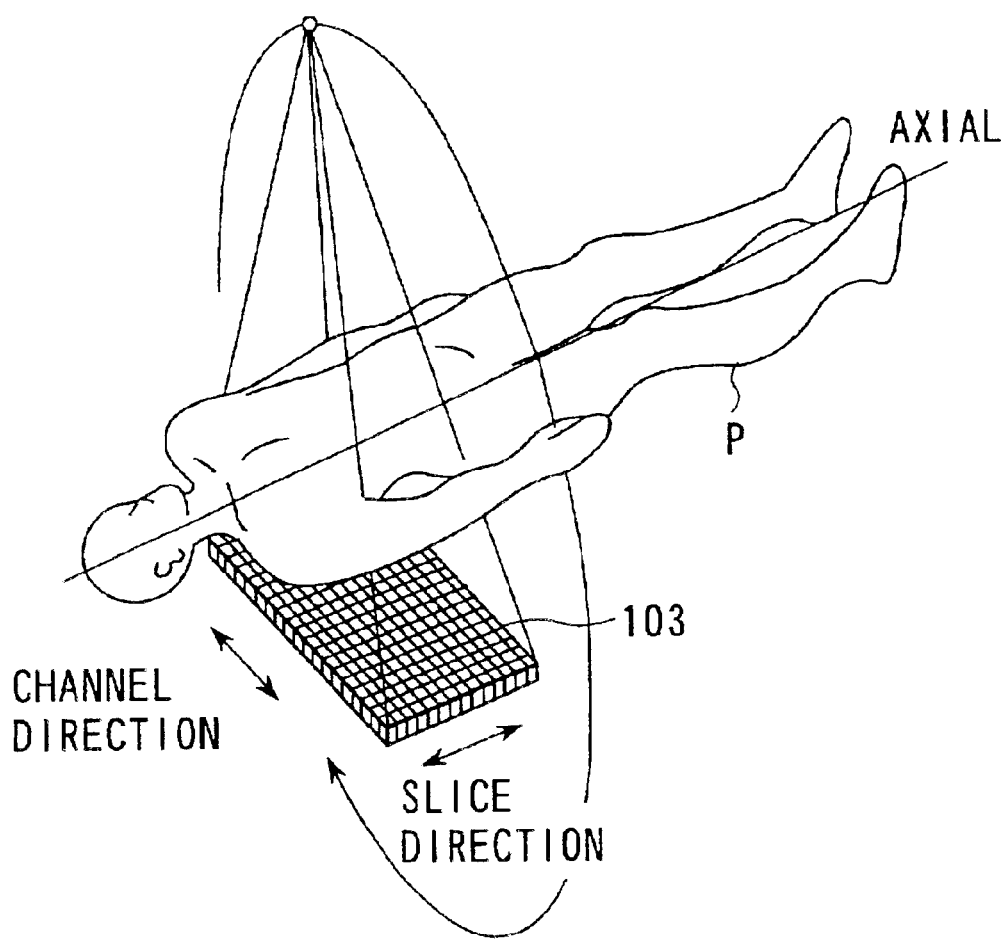
FIG. 27 is a perspective view of a radiation detector in FIG. 26.

FIG. 26 shows the arrangement of an x-ray CT apparatus according to this embodiment. FIG. 27 is a perspective view of the radiation detector in FIG. 26. A rotating ring 102 is rotated at a speed as high as one rotation per sec by a gantry driving unit 107. An x-ray tube 101 for generating an x-ray cone beam (rectangular pyramid) to an object P placed in an effective field-of-view region FOV is mounted on the rotating ring 102. A high-voltage generator 109 supplies power required for the radiation of x-rays to the x-ray tube 101 through a slip ring 108.

A radiation detector 103 for detecting x-rays transmitted through the object P is attached to the rotating ring 102 in a direction to oppose the x-ray tube 101. In the radiation detector 103, a plurality of detection elements, each constituted by a pair of scintillator piece and photodiode as described in the first embodiment, are arranged in the form of a matrix in the slice direction of the object and the channel direction perpendicular to the slice direction. For example, several thousand detection elements are arranged in the channel direction, whereas several hundred detection elements are densely arranged in the slice direction.

Enormous data about all the M×N channels detected by the radiation detector 103 (M×N channel data per view will be referred to as "2D projection data" hereinafter) are temporarily collected by a data acquisition circuit (DAS) 104 and transmitted altogether to the data processing unit on the stationary side through a noncontact-type data transmitting unit 105 using optical communication. Detecting operation by the radiation detector 103 is repeated e.g., about 1,000 times during one rotation (about one sec) to generate enormous 2D projection data corresponding to M×N channels 1,000 times per sec (rotation). To transmit such enormous 2D projection data, which are generated at high speed, without any time delay, the data acquisition circuit 104 and noncontact-type data transmitting unit 105 are designed to perform ultra-high speed processing.

The following components are mutually connected to the data processing unit through a data/control bus 300: a host controller 110 serving as a main unit, a pre-processing unit 106 for performing pre-processing such as data correction, a storing unit 111, a secondary storing unit 112, a data processing unit 113, a reconstructing unit 114, an input device 115, and a display unit 116. In addition, an external image processing unit 200 made up of a secondary storage unit 201, data processing unit 202, reconstructing unit 203, input device 204, and display unit 205 is connected to the data processing unit through the data/control bus 300.

Figure 28:
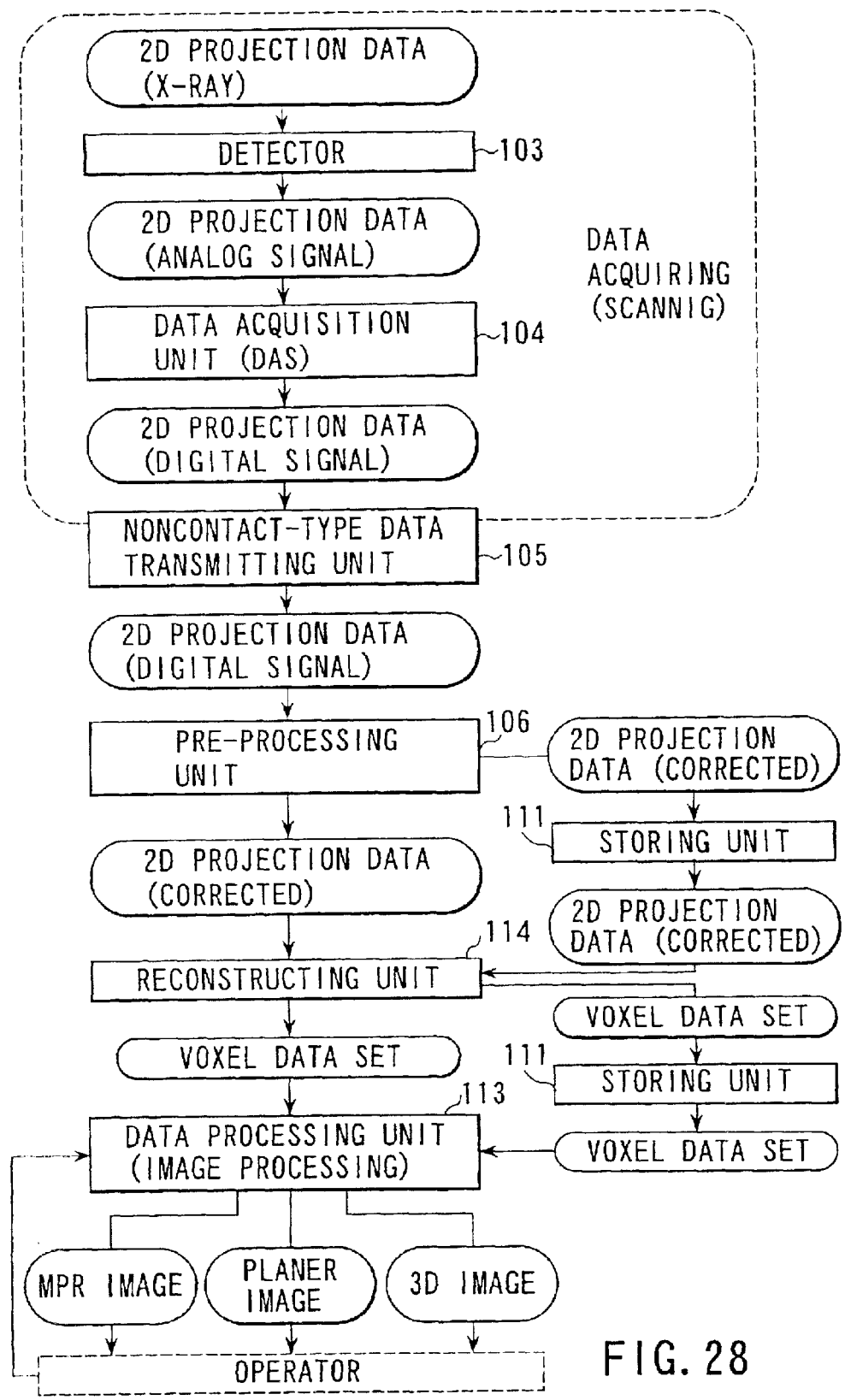
FIG. 28 is a view showing processing and the flow of data in the second embodiment.

FIG. 28 shows data processing and its flow. An x-ray beam transmitted through the object is converted into 2D projection data of an analog electrical signal by the radiation detector 103 and further converted into 2D projection data of a digital electrical signal by the data acquisition circuit 104. Thereafter, the data is sent through the noncontact-type data transmitting unit 105 to the pre-processing unit 106 for performing various correction operations. The 360° 2D projection data, i.e., 1,000 sets of 2D projection data, which have undergone sensitivity correction, x-ray intensity correction, and the like in the pre-processing unit 106 are sent to the reconstructing unit 114 directly or after temporarily stored in the storing unit 111. These data are then reconstructed into x-ray absorption coefficient 3D distribution data (to be referred to as "volume data (collection of voxel data)") in a wide target region (volume) in the slice direction according to a 3D image reconstruction algorithm represented by, for example, a so-called Feldkamp method. This 3D distribution data is typically reconstructed as a collection of multislice tomographic image data.

The reconstructed volume data is sent to the data processing unit 113 directly or after temporarily stored in the storing unit 111. This data is then converted into so-called pseudo-3D image data, e.g., a tomographic image of an arbitrary slice, a projection image from an arbitrary direction, or a 3D surface image of a specific organ which is obtained by rendering processing, in accordance with an instruction from an operator, and is displayed on the display unit 116.

Although data processing such as reconstruction and slice conversion and display operation are generally performed within an x-ray CT apparatus 100, these operations may be executed by the external image processing unit 200. When the external image processing unit 200 is to be used, data sent from the x-ray CT apparatus 100 to the image processing unit 200 does not interfere with the effects of this embodiment regardless of the state of the data, i.e., a state before reconstruction, a state after reconstruction, or a state immediately before display operation after data processing.

Although the voxel size of the above volume data changes depending on the size of one detection element of the radiation detector 103, the geometry of the system, the data acquisition speed, and the like, the minimum voxel size should be about 0.5 mm×0.5 mm×0.5 mm. The apparatus 100 equipping the detector of the first embodiment can acquire big size and isotropic volume data in one rotation. Further the voxel data is successively acquired in a wide region. Therefore, a resolution can be fixed between tomographic images for cross sections. This is advantage to a clinical diagnosis.

The operator of the system selects and sets one of the display forms descried above, i.e., a tomographic image of an arbitrary slice, a projection image from an arbitrary direction, and 3D surface display, which have already been widely practiced, in accordance with the purposes of an inspection and diagnosis. Images in different forms are generated from one volume data and displayed. Display modes include a mode of simultaneously displaying a plurality of types of images as well as a mode of displaying only one type of image. The operator can switch these modes in accordance with a purpose.

Figure 29:
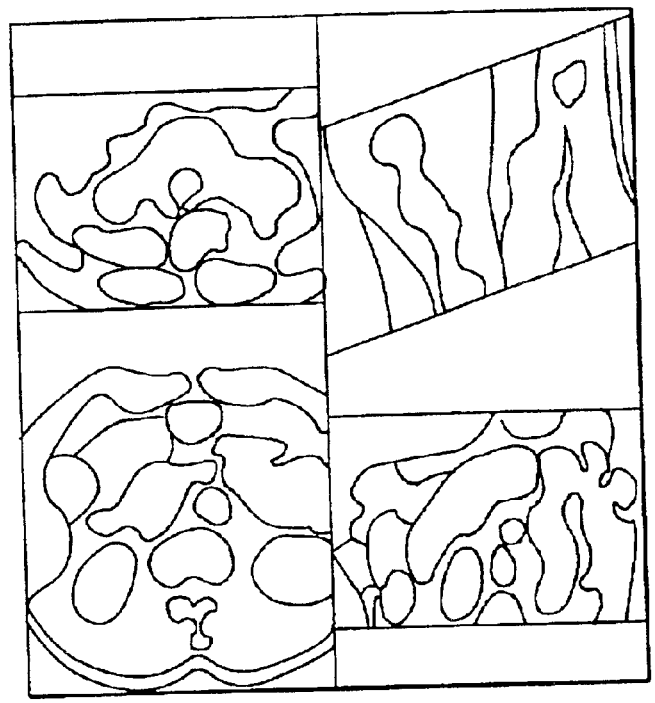
FIG. 29 is a view showing an example of image display in the second embodiment.

As shown in FIG. 29, in addition to a tomographic image of a slice (axial slice) perpendicular to the body axis which is obtained by conventional x-ray CT apparatus, tomographic images of arbitrary slices include tomographic images of slices perpendicular to the axial slice, e.g., a saggital plane and coronal plane, and tomographic images of slices oblique to these slices. Voxel data of a designated slice with a designated thickness are extracted from the above volume data and displayed altogether. A projection image from an arbitrary direction is used to display, for example, the maximum value and cumulative value of voxel data arranged in a set direction as a 2D image with respect to the volume data. 3D surface display is a method of extracting a surface with a set threshold and displaying the surface as a 3D image by shading based on a set light source. With this method, the operator can grasp an internal structure by observing while changing the threshold.

In 1-rotation scanning, by performing the above data processing, one volume data about a region of interest as wide as 30 cm in the slice direction can be obtained, without any time difference in the slice direction, from 2D projection data from many directions which are obtained by only one rotation. The operator can observe a tomographic image at a given time other than a tomographic image of an axial slice.

When the same processing as that in 1-rotation scanning is to be repeatedly performed for 2D projection data from many directions obtained by a plurality of rotations in continuous rotation scanning, a plurality of volume data are obtained instead of one volume data. Even if reconstruction is performed every rotation, data sets equal to the number of rotations can be obtained. In addition, by shifting the range (rotational angle range of the system) of data used for reconstruction little by little, many volume data that slightly differ in time can be obtained.

As in the case of 1-rotation scanning, as a display image form, one of the following forms: a tomographic image of an arbitrary slice, a projection image from an arbitrary direction, and 3D surface display, can be selected in accordance with the settings in the system which are made by the operator.

Figure 30:
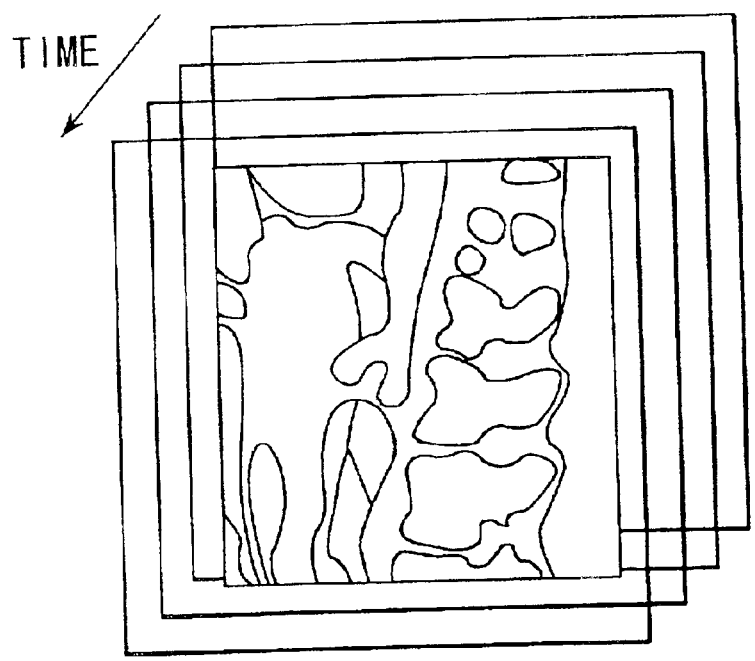
FIG. 30 is another example of image display in the second embodiment.

Images that slightly differ in time are generated in a set form from the above volume data that slightly differ in time, and sequentially displayed, as shown in FIG. 30. This allows the operator to observe the images in the set form in real time as moving images. Operation of displaying images as moving images concurrently with this continuous scanning will be referred to as CT fluoroscopy.

Figure 31:
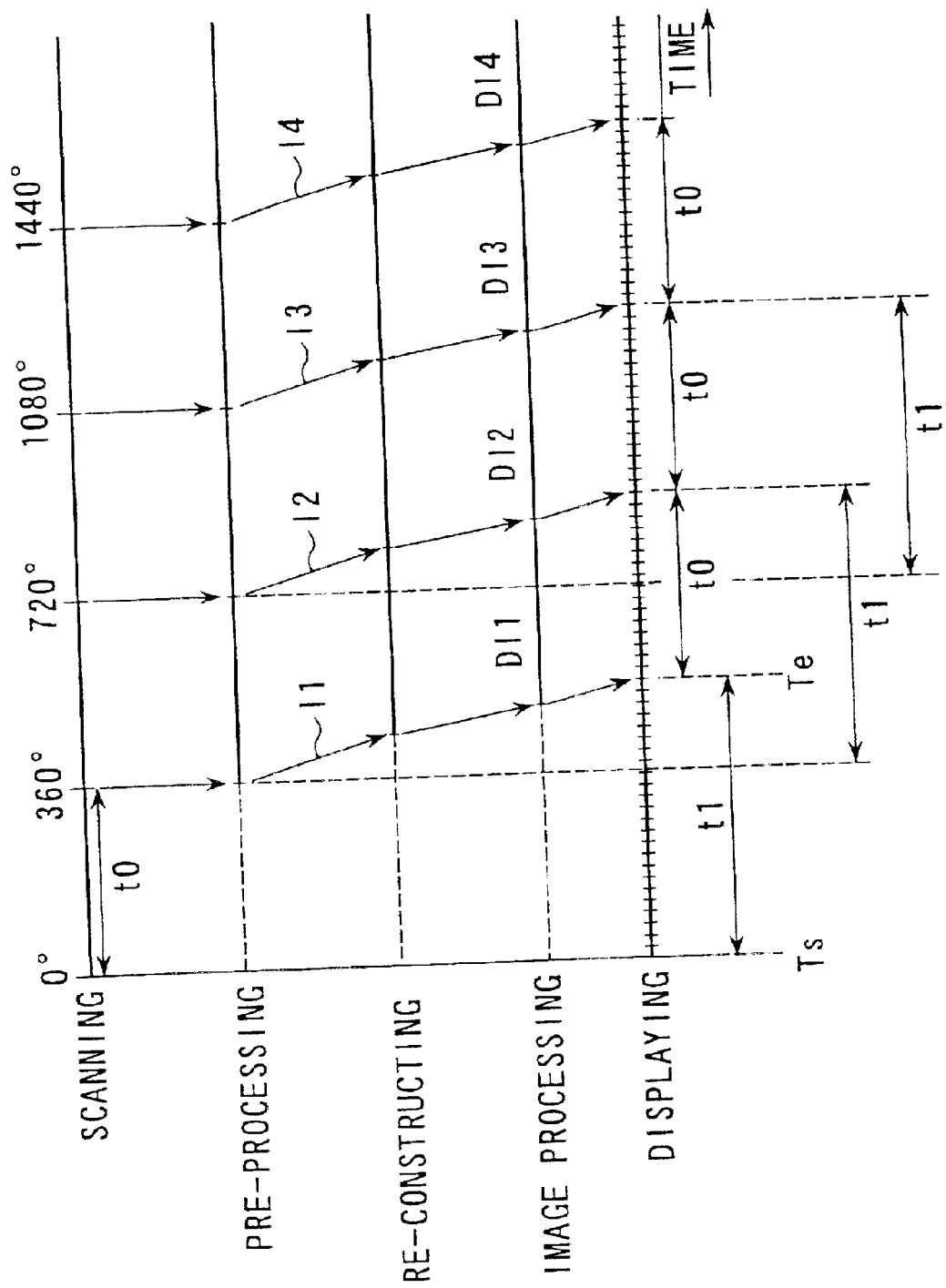
FIG. 31 is a view showing CT fluoroscopic operation in the second embodiment.

FIG. 31 shows the temporal flow from scanning in this CT fluoroscopy to image displaying on one time scale. Assume that the angular range of projection data required to reconstruct one 3D image data is 360°. Obviously, this range may be set to 180°+view angle. First of all, the x-ray tube 101 and radiation detector 103 continuously rotate around the object at high speed. The time required for one rotation is represented by t0. Projection data that are sequentially acquired are subjected to pre-processing almost in real time. The reconstructing unit 114 then reconstruct 3D image data "I" on the basis of the 360° projection data having undergone the pre-processing. The data processing unit 113 generates image data "DI" of a tomographic image of an arbitrary slice, a projection image from an arbitrary direction, 3D surface image, or the like on the basis of the reconstructed 3D image data "I". This image data "DI" is displayed on the display unit 116.

In CT fluoroscopy, a series of operations from scanning to image displaying are concurrently performed, and images are sequentially reconstructed while continuous scanning is performed. These images are sequentially displayed to be displayed as moving images.

To implement this CT fluoroscopy, the reconstructing unit 114 has the performance required to reconstruct the 3D image data I within a time shorter than the time t0 required to acquire projection data corresponding to a predetermined angular range (360° in this case) concurrently with acquisition operation of projection data (scanning). The data processing unit 113 has the performance required to generate the display image data DI from 3D image data within a time shorter than the reconstruction time for the 3D image data I. The display unit 116 has a counter, memory, and the like which are required to start displaying the image data DI a predetermined-time after a start point Ts or end point Te of an interval of acquisition operation of projection data from which the image data DI originates.

To facilitate observation of images as moving images, this apparatus further includes the following means.

(1) Displaying can be performed not only in the forward direction but also in the reverse direction (reverse playback).

(2) An automatic-updating mode or manual updating mode can be selected as an image updating (switching) mode, and image switching can be done even during display operation.

(3) In the automatic updating mode, the operator designates a start point (moving image playback start point) and end point (moving image playback end point), and image updating is done at a predetermined updating speed (image switching speed (moving image playback speed)).

(i) The start and end points can be changed even during display operation.
    (ii) The predetermined updating speeds include the following modes:
        (a) actual time intervals based on the scanning speed and reconstruction intervals;
        (b) slow display
        (c) frame display
        (d) fast (double-speed) display
    (iii) In addition to preset speeds, displaying is performed at an arbitrary speed set by the operator.
    (iv) Updating speed can be changed even during display operation.
    (v) When displaying is done up to the end point, displaying is repeated from the start point.

(4) In the manual updating mode, updating is performed in accordance with the operation performed by the operator.

To easily grasp the relationship between overall movement and an image that is being displayed, all or some of images in the overall time range can be displayed as index images concurrently with a main image.

(1) The time of a main image is displayed on an index image. The time of the main image is set on the index image and the playback start point of a moving image is switched to another point.

(2) Index images can be obtained by reducing images or decreasing the resolution of images in the data processing unit 113, and a plurality of index images are simultaneously displayed in one window as a list.

(3) Index images are not generated and displayed with respect to all images as targets, but a plurality of images in the playback period are properly thinned out and selected.

(i) Images are thinned out and displayed at predetermined time intervals.

(ii) A portion corresponding to a fast motion between images is extracted and displayed.

(4) Index images are used to display the time zones before and after a main image and updated as the main image is updated.

Information that changes with time, e.g., the CT value of an ROI or electrocardiogram, is displayed in the form of a graph, concurrently with main image displaying, and the time of the main image is also displayed on the graph that is being displayed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An x-ray CT apparatus, comprising:
    a gantry including:
        an x-ray source which generates an x-ray cone beam,
        a radiation detector having a plurality of element blocks, each element block having a plurality of detection elements which are arranged in a matrix form and which detect x-rays transmitted-through an object, and
        a rotating device which allows the x-ray source and the radiation detector to rotate continuously to permit said gantry to continuously acquire projection data on the object; and
    a reconstructing unit which reconstructs volume data acquired at an arbitrary timing, on the basis of the projection data,
    wherein each of said plurality of element blocks is formed on a corresponding one of a plurality of block substrates, said plurality of block substrates are formed in a direction parallel to a rotational axis of the radiation detector to obtain each of a plurality of modules, and said plurality of modules are arranged in a direction perpendicular to the rotational axis of the radiation detector on a base of the radiation detector.

2. An x-ray CT apparatus according to claim 1, wherein said gantry acquires projection data items corresponding to a plurality of timings; and
    said reconstructing unit reconstructs volume data items corresponding to the plurality of timings.

3. An x-ray CT apparatus according to claim 1, wherein said volume data is a collection of isotropic voxel data.

4. An x-ray CT apparatus according to claim 1, wherein said plurality of element blocks are each arranged on block substrates further arranged on a plurality of module bases that are included in a plurality of detector modules that are arrange on a base of the radiation detector.

5. An x-ray CT apparatus according to claim 1, wherein the element blocks of the radiation detector are arranged in such a manner as to form a polygon as viewed in a direction perpendicular to the rotational axis of the radiation detector, and are arranged substantially in a plane as viewed in a direction parallel to the rotational axis of the radiation detector.

6. An x-ray CT apparatus according to claim 1, wherein the element blocks of the radiation detector are arranged in such a manner as to form an arc, with a focal point of the x-ray source as a center, as viewed in a direction perpendicular to the rotational axis of the radiation detector.

7. An x-ray CT apparatus according to claim 5, wherein each of said element blocks includes:
    a semiconductor substrate;
    a plurality of photodiodes formed on the semiconductor substrate and arranged in a matrix pattern; and
    a scintillator block provided on the photodiodes.

8. An x-ray CT apparatus according to claim 4, wherein each of the detector modules includes a data collecting circuit which collects signals from the detection elements.

9. An x-ray CT apparatus according to claim 8, wherein said data collecting circuit includes an amplifier and an analog/digital converter.

10. An x-ray CT apparatus according to claim 4, wherein each of said plurality of detector modules is detachably provided on the detector base.

11. An x-ray CT apparatus according to claim 7, wherein said scintillator block includes a scintillator niece located, at an end as viewed in the direction parallel to the rotational axis of the radiation detector, and the scintillator piece includes a space which arranges wiring connecting the photodiodes to the substrate.

12. An x-ray CT apparatus according to claim 4, wherein said detector modules are attached to corresponding collimator modules.

13. An x-ray CT apparatus according to claim 12, wherein said collimator modules include collimator plates, and the detection elements of the detector modules are greater in number than the collimator plates.

14. An x-ray CT apparatus according to claim 13, wherein said collimator modules include a first collimator module and a second collimator module which share a predetermined collimator plate.

15. An x-ray CT apparatus according to claim 7, wherein said photodiodes are arranged in a matrix form of m×n, and comprise m photodiodes which are arrayed in a body axis direction of the object and which include output terminals connected to a common signal line, and n switch elements gates arrayed in the direction perpendicular to the rotational axis of the radiation detector and connected to a common control line.

16. An x-ray CT apparatus according to claim 15, wherein said signal line is connected to the output terminals at a position between the element blocks of the detector modules.

17. An x-ray CT apparatus according to claim 15, further comprising a read control circuit provided on the substrate, said read control circuit controlling an ON/OFF operation of the switching elements and reading out signals from the detection elements.

18. An array CT apparatus according to claim 17, wherein said read control circuit sequentially turns on the switching elements along the signal line with respect to the plurality of element blocks in said detector module.

19. An x-ray CT apparatus according to claim 17, wherein said read control circuit sequentially turns on the switching elements along the signal line, and executes the sequential operation between the plurality of element blocks in said detector module with a predetermined time shift such that signal reads of element blocks in said detector module are interleaved in an interval of a signal read of the a given element block in said detector module.

20. An x-ray CT apparatus according to claim 17, wherein said read control circuit executes operations of sequentially turning on the switching elements along the signal line in parallel with respect to the plurality of element blocks in said detector module.

21. An x-ray CT apparatus according to claim 1, wherein the plurality of detection elements are arranged parallel and perpendicular to the rotational axis of the radiation detector.

* * * * *